US009334308B2

(12) United States Patent
Moroz

(10) Patent No.: US 9,334,308 B2
(45) Date of Patent: May 10, 2016

(54) PLIF MULTIMERIC PEPTIDES AND USES THEREOF

(71) Applicant: Ramot at Tel-Aviv University Ltd., Tel-Aviv (IL)

(72) Inventor: Chaya Moroz, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 159 days.

(21) Appl. No.: 13/792,102

(22) Filed: Mar. 10, 2013

(65) Prior Publication Data

US 2013/0252905 A1    Sep. 26, 2013

Related U.S. Application Data

(60) Provisional application No. 61/614,110, filed on Mar. 22, 2012.

(51) Int. Cl.
| | | |
|---|---|---|
| *C07K 14/01* | (2006.01) | |
| *C07K 14/00* | (2006.01) | |
| *C07K 7/08* | (2006.01) | |
| *C07K 14/47* | (2006.01) | |
| *A61K 38/00* | (2006.01) | |
| *A61K 39/00* | (2006.01) | |

(52) U.S. Cl.
CPC .................. *C07K 14/001* (2013.01); *C07K 7/08* (2013.01); *C07K 14/47* (2013.01); *A61K 38/00* (2013.01); *A61K 39/00* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,882,270 A | 11/1989 | Moroz | |
| 7,217,686 B1 * | 5/2007 | Moroz | ......................... 514/16.8 |

FOREIGN PATENT DOCUMENTS

| | | |
|---|---|---|
| WO | WO 2013/140389 | 9/2013 |
| WO | WO 2014/118785 | 8/2014 |

OTHER PUBLICATIONS

Moroz et al. "PLIF, A Novel Human Ferritin Subunit From Placenta With Immunosuppressive Activity", The Journal of Biological Chemistry, 277(15): 12901-12905, Apr. 12, 2002.
International Search Report and the Written Opinion Dated Jun. 24, 2013 From the International Searching Authority Re. Application No. PCT/IL2013/050218.
Halpern et al. "Antibodies to Placental Immunoregulatory Ferritin with Transfer of Polyclonal Lymphocytes Arrest MCF-7 human Beast Cancer Growth in a Nude Mouse Mode", Neoplasia 9(6): 487-494, Jun. 2007. Abstract, p. 487 (last para), 492-493, Figs. 7,8.
Nahum et al. "Blocking of the Placental Immune-Modulatory Ferritin Activates Th1 Type Cytokines and Affects Placenta Development, Fetal Growth and the Pregnancy Outcome", Human Reproduction, 19(3): 715-722, 2004. Abstract, p. 717-720, Fig.6.

* cited by examiner

*Primary Examiner* — Michael Szperka

(57) ABSTRACT

Provided is a multimeric peptide comprising at least two peptide monomers linked to one another, each of the at least two peptide monomers comprising at least 6 consecutive amino acids from the amino acid sequence as set forth in SEQ ID NO: 1, wherein the at least two peptide monomers are each no longer than 30 amino acids, wherein the multimeric peptide is capable of reducing binding of Placenta Immunomodulatory Factor (PLIF) to human leukocytes.

25 Claims, 22 Drawing Sheets
(20 of 22 Drawing Sheet(s) Filed in Color)

┌ Cys-Gly-His-His-Leu-Leu-Arg-Pro-Arg-Arg-Arg-Lys-Arg-Pro-His-Ser-Ile-Pro-Thr-Pro-Ile-Leu-Ile-Phe-Arg-Ser-Pro-OH
└ Cys-Gly-His-His-Leu-Leu-Arg-Pro-Arg-Arg-Arg-Lys-Arg-Pro-His-Ser-Ile-Pro-Thr-Pro-Ile-Leu-Ile-Phe-Arg-Ser-Pro-OH

Purity: ≥ 95% by HPLC

Mass Spectra: Calculated: 6481.8
              Found:      6482.4

FIG. 3

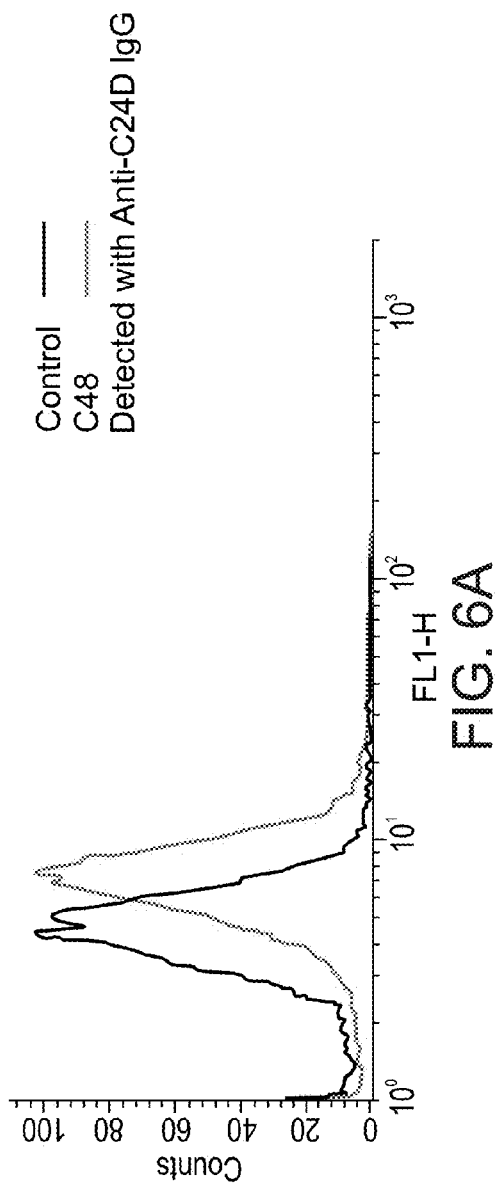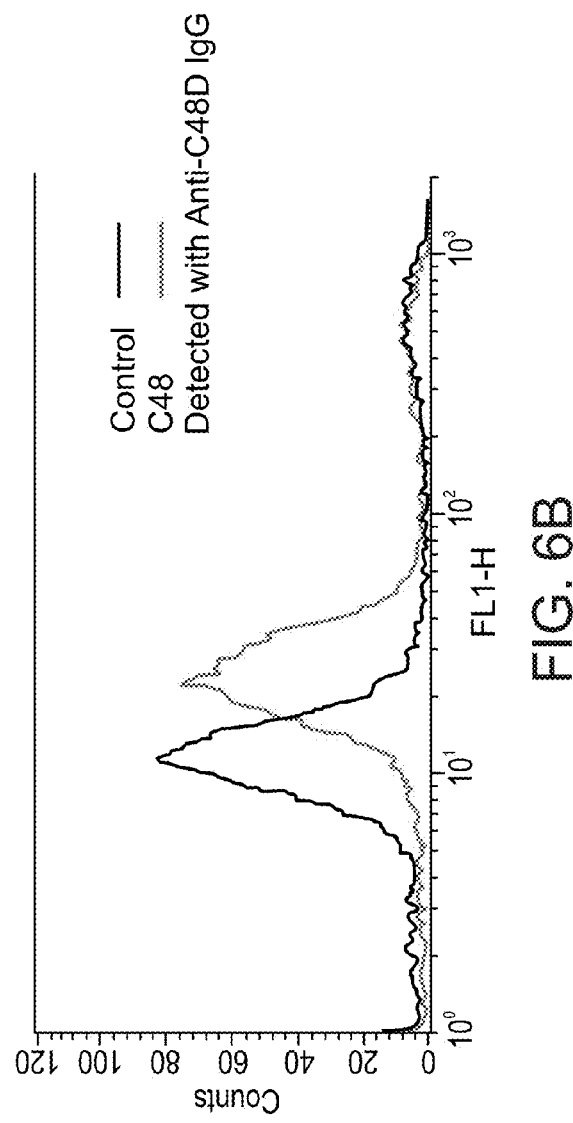
FIG. 6A
FIG. 6B

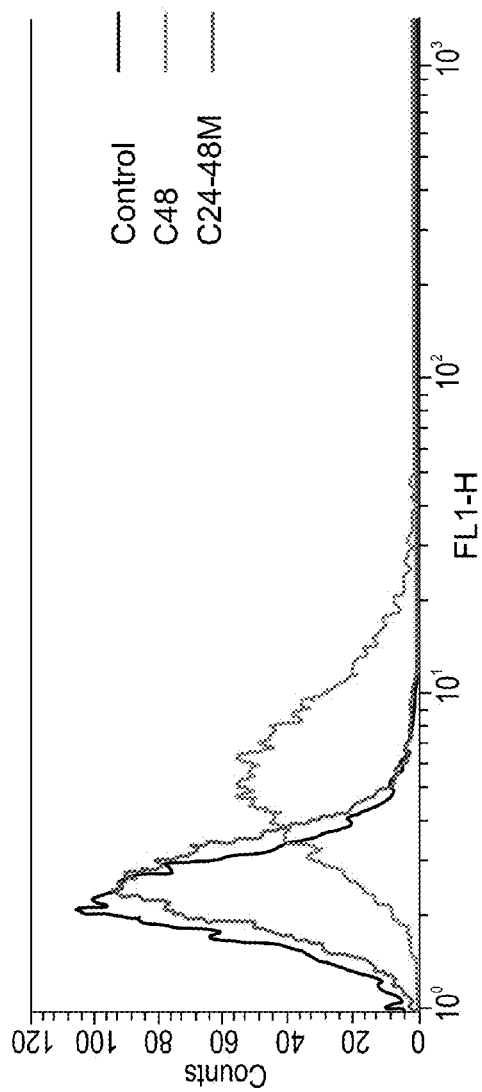
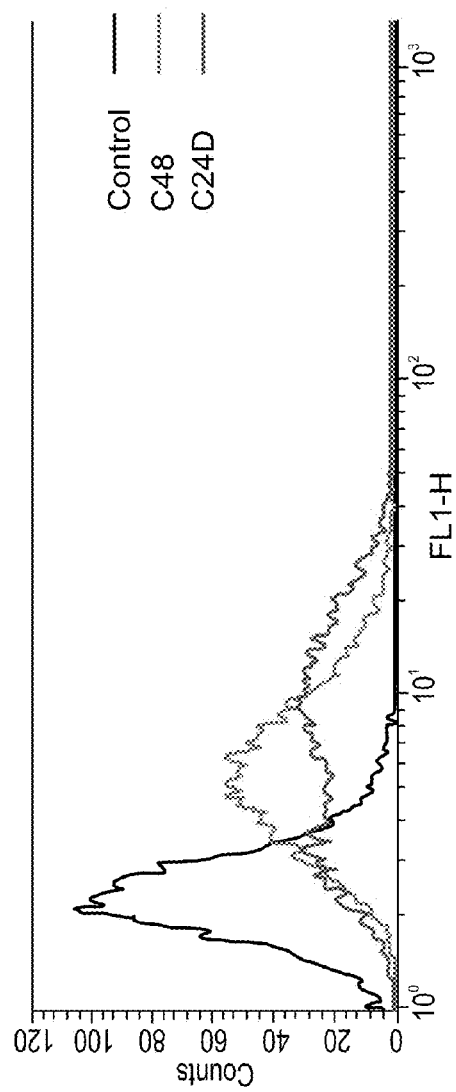

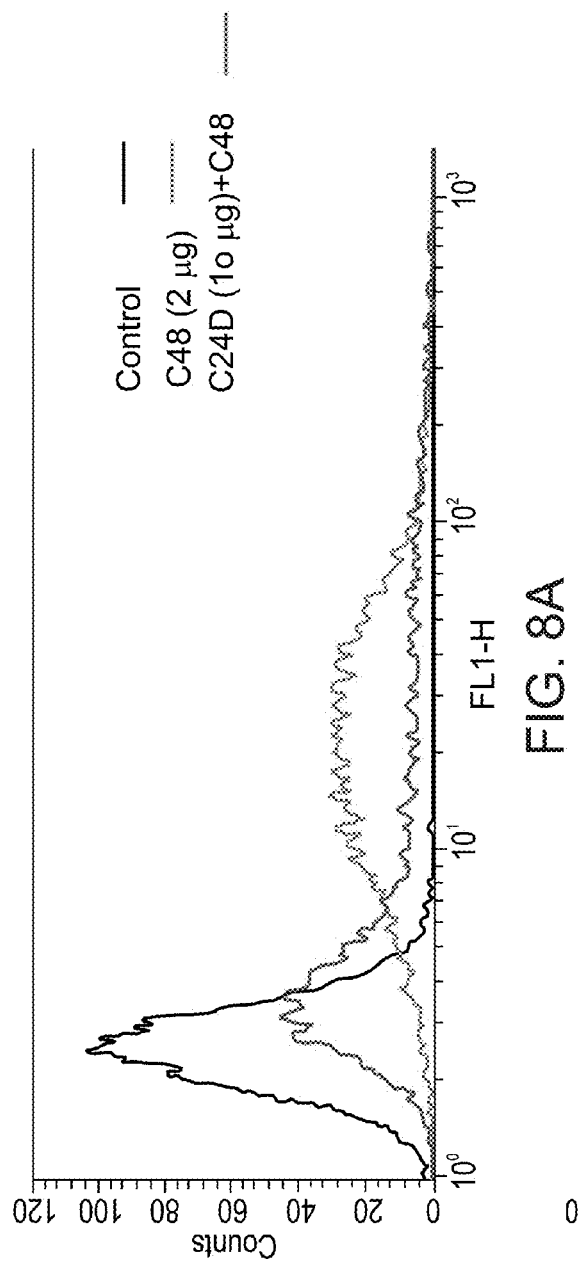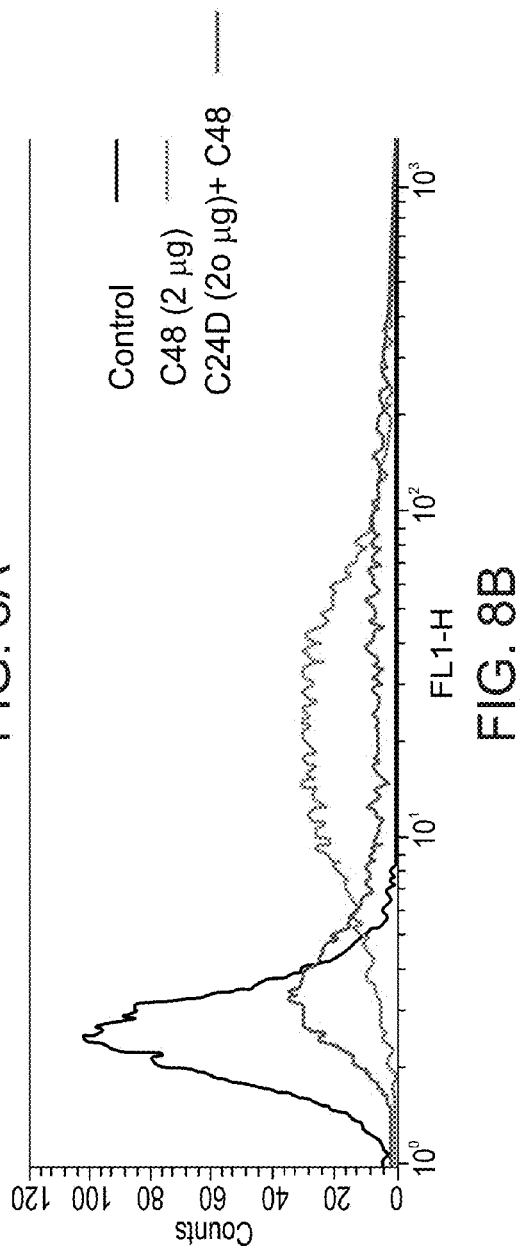
FIG. 8A
FIG. 8B

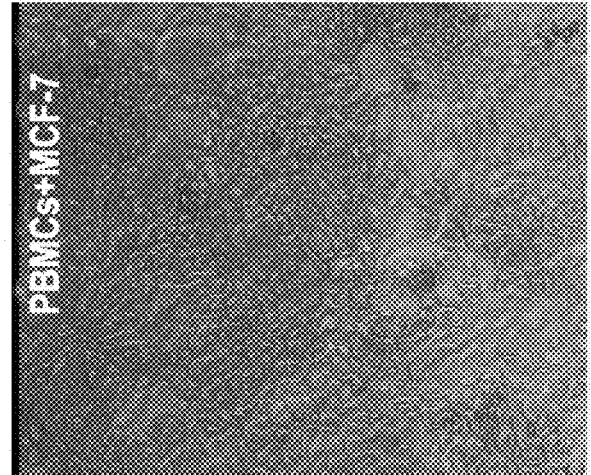
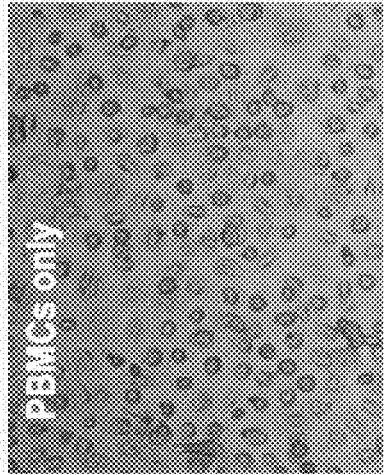
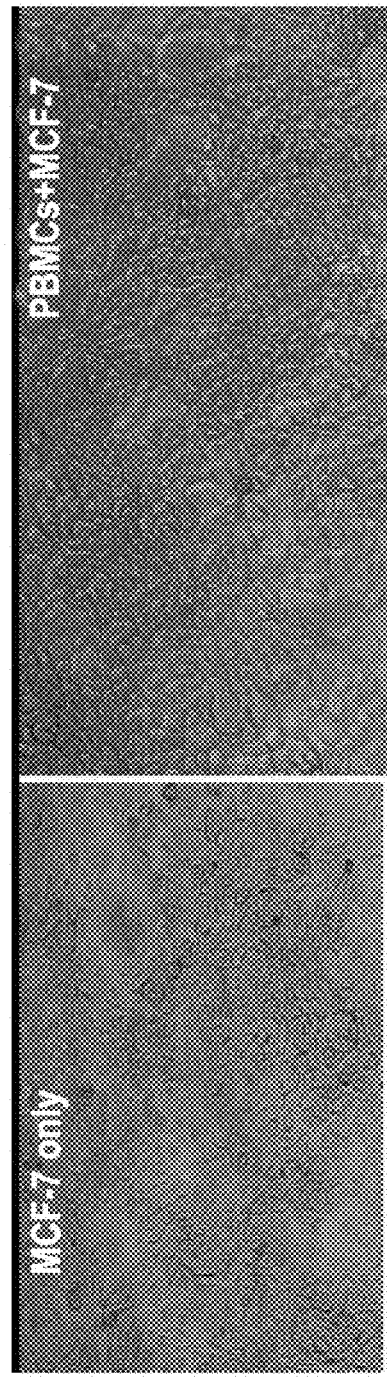

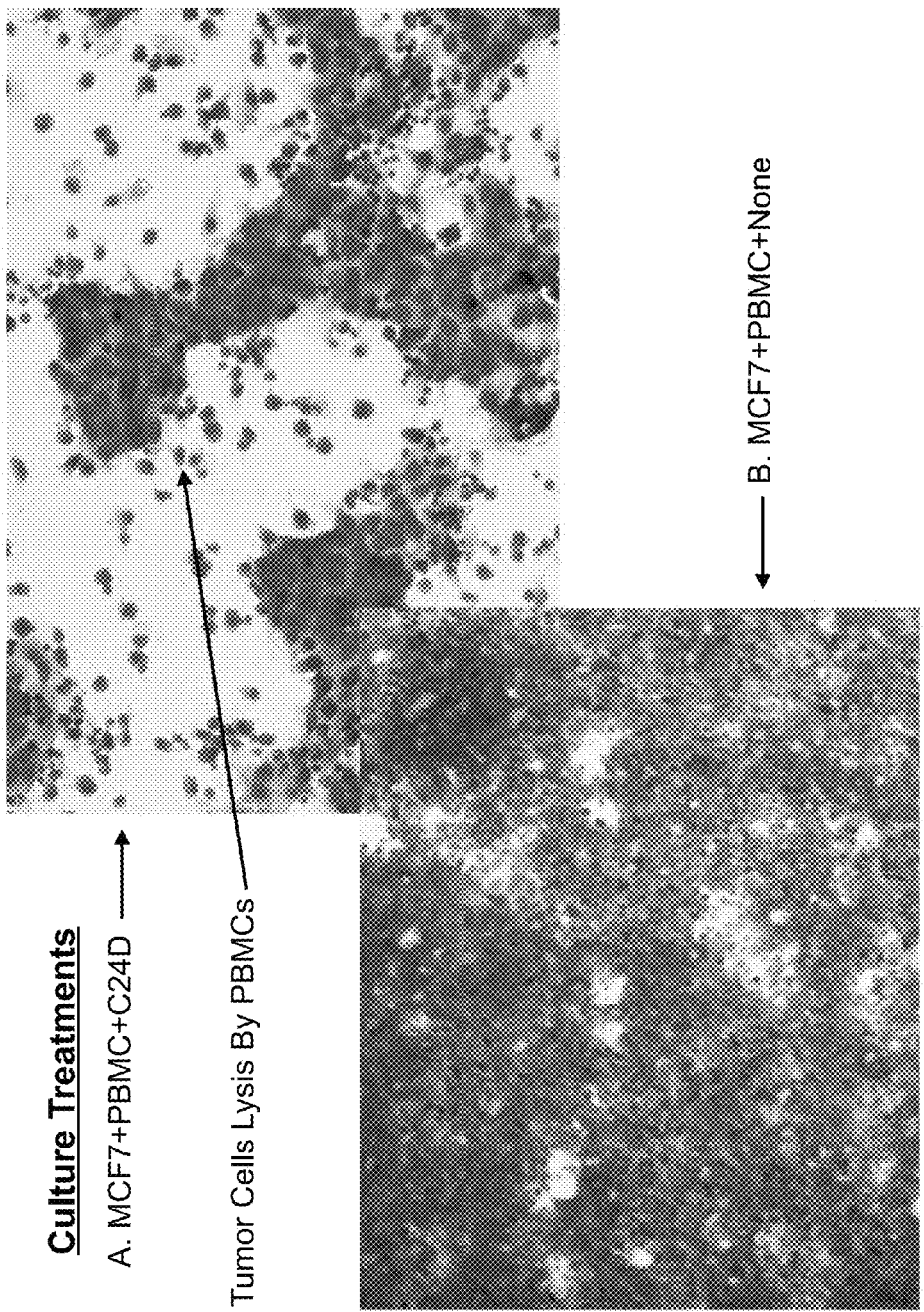

Control 1
From Untreated Culture

Control-2 PBMConly +C24D-30μgr./ml

From C24D (30 mgr./ml) treated Culture

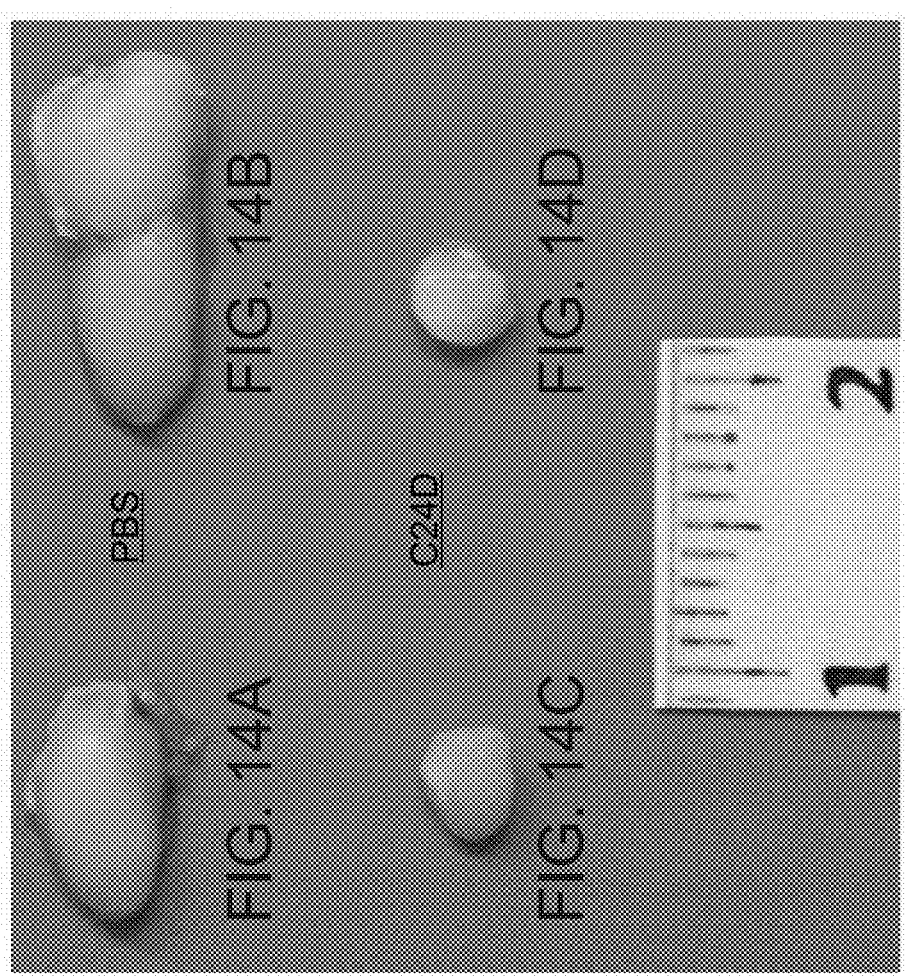

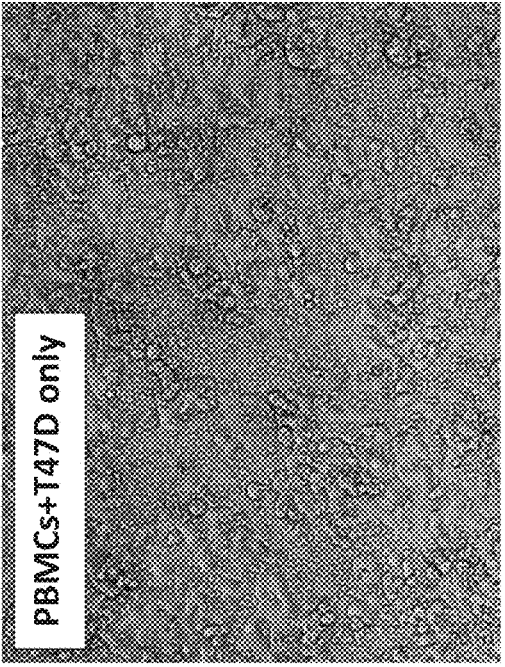
FIG. 17B PBMCs+T47D only
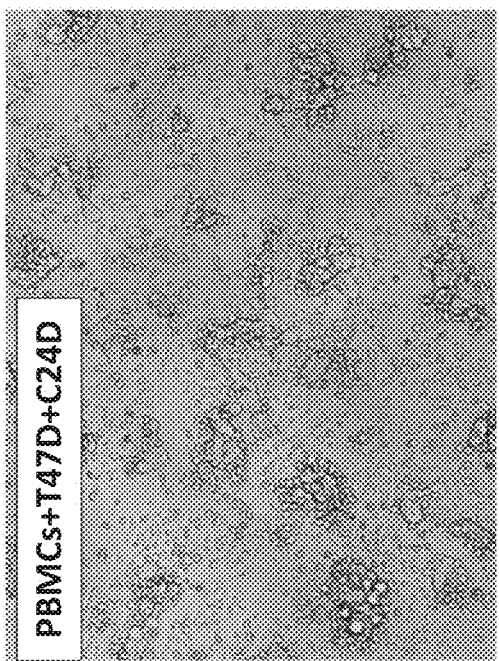
FIG. 17C PBMCs+T47D+C24D
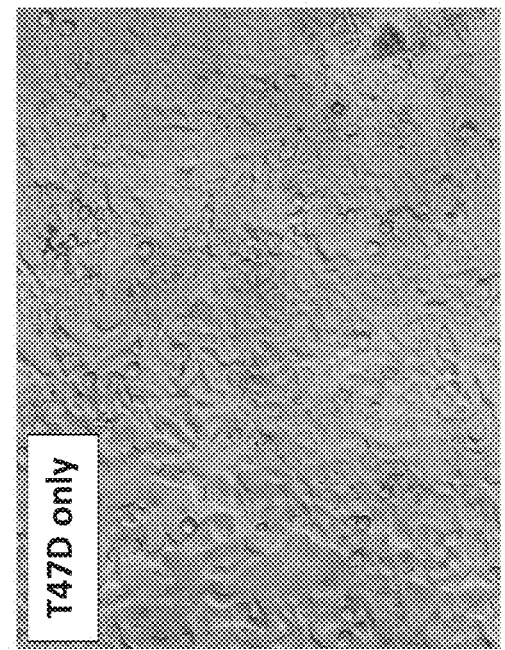
FIG. 17A T47D only

PLIF MULTIMERIC PEPTIDES AND USES THEREOF

RELATED APPLICATION

This application claims the benefit of priority under 35 USC §119(e) of U.S. Provisional Patent Application No. 61/614,110 filed Mar. 22, 2012, the contents of which are incorporated herein by reference in their entirety.

SEQUENCE LISTING STATEMENT

The ASCII file, entitled 55642SequenceListing.txt, created on Mar. 10, 2013, comprising 22,656, bytes, submitted concurrently with the filing of this application is incorporated herein by reference.

FIELD AND BACKGROUND OF THE INVENTION

The present invention, in some embodiments thereof, relates to a multimeric peptide and, more particularly, but not exclusively, to a dimer comprising a Placental Immunoregulatory Ferritin (PLIF) amino acid sequence which is useful for the treatment of cancer.

Placenta Immunomodulatory Factor (PLIF) is a protein composed of 165 amino acids. Of these, 117 match the ferritin heavy chain sequence, whereas the C-terminal 48 amino acids (C48) has a sequence which is not related to ferritin. It has been shown that the subcloned recombinant C48 peptide exhibits the bioactivity and therapeutic properties of PLIF [Moroz et al, J. Biol. Chem. 2002, 277, 12901-12905].

PLIF is expressed in the feto-maternal interface in both decidual mononuclear cells and syncytiotrophoblast cells. C48/PLIF binds to macrophages and activated T cells, inducing high levels of IL-10, and acts as a regulatory cytokine. It governs the balance between Th1/Th2 cytokines, which is essential for induction of tolerance during pregnancy. A significantly high correlation was observed between low levels of serum PLIF and the different pathological pregnancy conditions: early pregnancy failures; pregnancies complicated with abortion; intrauterine growth restriction (IUGR); and women at risk for developing pre-eclampsia.

Vaccination of mice with C48 (the bioactive domain of PLIF) prior to mating prevented pregnancy development (immune contraceptive), providing further evidence for the major role of PLIF in in vivo immune regulation. Further, in pregnant mice, neutralization of PLIF in vivo by passive transfer of anti-C48 antibodies (daily injections), starting at 3.5 days post-coitum, resulted in high embryo resorption rate, placental and embryonic growth restriction without affecting embryo organogenesis. This was accompanied by a significantly increased secretion of INF-γ and IL-12 (Th1) cytokines known to interfere with pregnancy outcome.

Thus, PLIF may be viewed as a major regulatory cytokine governing the Th1/Th2 cytokine balance and suppressor Tr cells, essential for induction of tolerance during pregnancy.

Further experimental studies on the immune regulatory function of PLIF/C48 in human bone marrow cells revealed that C48/PLIF exhibited growth of bone marrow myeloid progenitor cells concomitantly with T cell suppression. This was due to its dual regulatory effect on the cytokine chemokine network. Thus, C48/PLIF has proven to be a novel bifunctional therapeutic modality which enabled successful allogeneic bone marrow transplantation with long lasting tolerance.

It was reasoned that tumor cells may activate and use the above immunosuppressive mechanism, resembling those in the placenta, which prevent rejection of the embryo, and thereby enable tumor growth. Indeed, it has been shown that PLIF is upregulated and expressed in malignant cells such as Hodgkin's and non-Hodgkin's lymphoma, acute lymphatic leukemia (ALL), human breast cancer tissues, and breast cancer cell lines (T47D and MCF-7), but not in benign breast disease. Similar to the embryo, PLIF manipulates the cytokine network and immune response, enabling immune escape.

Experiments have been performed to restore T cell immunity and induce rejection of breast cancer by neutralizing C48/PLIF. Rabbit anti-C48 polyclonal antibodies injected intraperitoneally (i.p.) into immune compromised Nude mice engrafted with MCF-7 human breast cancer cells resulted in growth arrest associated with human cell apoptosis and massive intra-tumor lymphocytic infiltration. This was accompanied by activation of INF-γ, thus affecting the cytokine network and leading to breakdown of tolerance.

Additional background art includes U.S. Pat. No. 4,882,270 which discloses a method for detecting breast cancer, by using antibodies against isoferritin placental protein.

U.S. Pat. No. 7,217,686 discloses the amino acid sequence of the 48 amino acid peptide of PLIF.

SUMMARY OF THE INVENTION

According to an aspect of some embodiments of the present invention there is provided a multimeric peptide comprising at least two peptide monomers linked to one another, each of the at least two peptide monomers comprising at least 6 consecutive amino acids from the amino acid sequence as set forth in SEQ ID NO: 1, wherein the at least two peptide monomers are each no longer than 30 amino acids, wherein the multimeric peptide is capable of reducing binding of Placenta Immunomodulatory Factor (PLIF) to human leukocytes.

According to some embodiments of the invention, the peptide is capable of increasing INF-γ secretion from activated leukocytes.

According to some embodiments of the invention, the multimeric peptide being a dimer.

According to some embodiments of the invention, each of the at least two peptide monomers comprise no more than 15 consecutive amino acids from the amino acid sequence as set forth in SEQ ID NO: 1.

According to some embodiments of the invention, the at least two peptide monomers comprise an identical amino acid sequence.

According to some embodiments of the invention, the peptide comprises each of the at least two peptide monomers the amino acid sequence as set forth in SEQ ID NO: 1.

According to some embodiments of the invention, each of said at least two peptide monomers comprise the amino acid sequence as set forth in SEQ ID NO: 101.

According to some embodiments of the invention, the multimeric peptide is for use in treating a disease associated with a TH2:TH1 bias.

According to some embodiments of the invention, the method further comprises detecting a level of PLIF in a sample of the subject prior to the treating.

According to some embodiments of the invention, the method further comprises detecting a level of PLIF in a sample of the subject following the treating.

According to some embodiments of the invention, the sample comprises a tumor sample or a blood sample.

According to some embodiments of the invention, the detecting is effected on the protein level.

According to some embodiments of the invention, the detecting is effected on the polynucleotide level.

According to some embodiments of the invention, each of the at least two peptide monomers is attached to a Cysteine (Cys) residue.

According to some embodiments of the invention, the carboxy end of the at least two peptide monomers is attached to the Cys residue.

According to some embodiments of the invention, each of the two peptide monomers are attached via a non-peptide linker.

According to some embodiments of the invention, the at least two peptide monomers are linked to one another by a disulfide bond.

According to some embodiments of the invention, the disulfide bond is an intermolecular disulfide bond formed between the Cys residues.

According to some embodiments of the invention, the multimeric peptide further comprises a Gly residue connecting the Cys residue to the carboxy end of the at least two peptide monomers.

According to some embodiments of the invention, each of the two at least two peptide monomers comprises the sequence selected from the group consisting of SEQ ID NOs: 2-7.

According to some embodiments of the invention, each of the at least two peptide monomers consists of the sequence selected from the group consisting of SEQ ID NOs: 8-13.

According to some embodiments of the invention, the multimeric peptide comprises at least one synthetic amino acid.

According to some embodiments of the invention, the at least two peptide monomers comprises least three peptide monomers.

According to some embodiments of the invention, the at least two peptide monomers are covalently linked to one another.

According to an aspect of some embodiments of the present invention there is provided a pharmaceutical composition comprising the dimeric peptide as an active agent and a pharmaceutically acceptable carrier.

According to an aspect of some embodiments of the present invention there is provided a pharmaceutical composition comprising the peptide as an active agent and a pharmaceutically acceptable carrier.

According to an aspect of some embodiments of the present invention there is provided a method of treating a disease associated with a TH2:TH1 bias, the method comprising administering a therapeutically effective amount of the dimeric to a subject in need thereof, thereby treating the disease associated with a TH2:TH1 bias.

According to some embodiments of the invention, the disease is cancer.

According to some embodiments of the invention, the treating results in cancer immunotherapy and long term anti-cancer immunity.

According to some embodiments of the invention, the cancer is selected from the group consisting of Hodgkin's lymphoma, non-Hodgkin's lymphoma, acute lymphatic leukemia (ALL) and breast cancer.

According to some embodiments of the invention, the disease is a retrovirally mediated disease.

According to some embodiments of the invention, the retrovirally mediated disease is HIV.

According to an aspect of some embodiments of the present invention there is provided an isolated peptide comprising at least 6 consecutive amino acids and no more than 30 amino acids from the amino acid sequence as set forth in SEQ ID NO: 1, wherein when linked to a second peptide comprising at least 6 consecutive amino acids and no more than 30 amino acids from the amino acid sequence as set forth in SEQ ID NO: 1 as a dimer, the dimer is capable of reducing binding of Placenta Immunomodulatory Factor (PLIF) to human leukocytes.

According to an aspect of some embodiments of the present invention there is provided a method of generating the dimeric peptide, the method comprising linking two isolated peptides, which each of the at least two isolated peptides comprise at least 6 consecutive amino acids and no more than 30 amino acids from the amino acid sequence as set forth in SEQ ID NO: 1, thereby generating the dimeric peptide of claim 1.

According to an aspect of some embodiments of the present invention there is provided an isolated antibody which binds to the mutimeric peptide of claim 1, wherein the affinity of the antibody for the multimeric peptide is higher than the affinity of the antibody for C48 under identical conditions.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a graph illustrating the binding of Anti-C24D IgG to C48 and to C24D.

FIG. 2 is a graph illustrating anti-C48 IgG binding to C48 and C24D.

FIG. 3 illustrates the sequence of synthetic C24D polypeptide (SEQ ID NO: 102).

FIG. 4 is a schematic illustration of the C24D synthetic polypeptide in relation to PLIF and C48.

FIG. 5 is an HPLC chromatogram of C24D.

FIGS. 6A-B are graphs illustrating the binding of C48 to human macrophages as detected by Rabbit-anti-C48 and by Mouse-anti-C24D.

FIGS. 7A-B are graphs comparing the binding of C48, C24-48M, and C24D to HDMAR human T cell line (detected by anti-C24D IgG).

FIGS. 8A-B are graphs illustrating the inhibition of C48 binding to HDMAR human T cells by different concentrations of C24D (detected by anti-C48 IgG).

Figure 9:
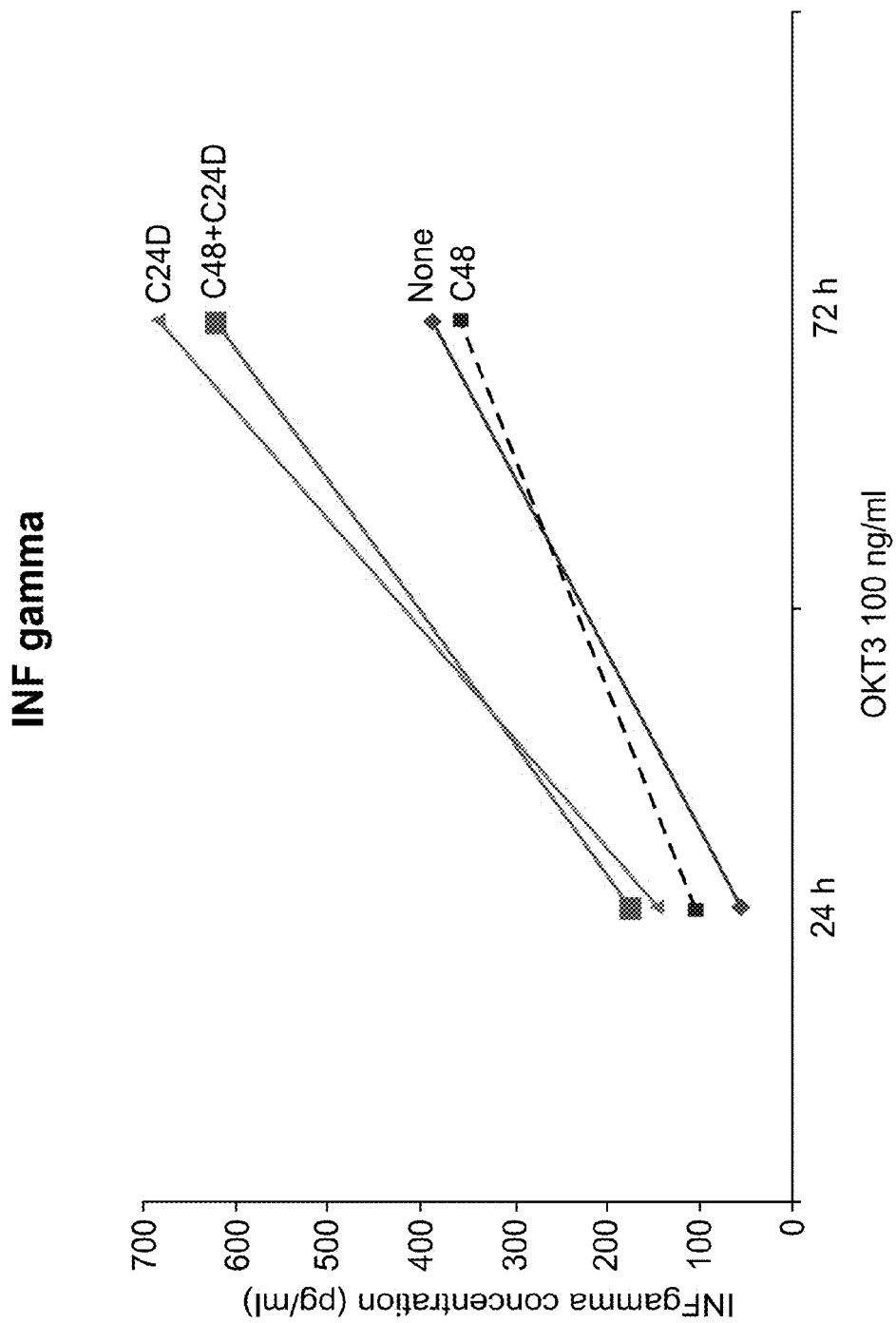

FIG. 9 is a graph illustrating the effect of C24D on interferon γ secretion by human PBMCs activated with the immunosuppressant drug OKT3.

Figure 10:
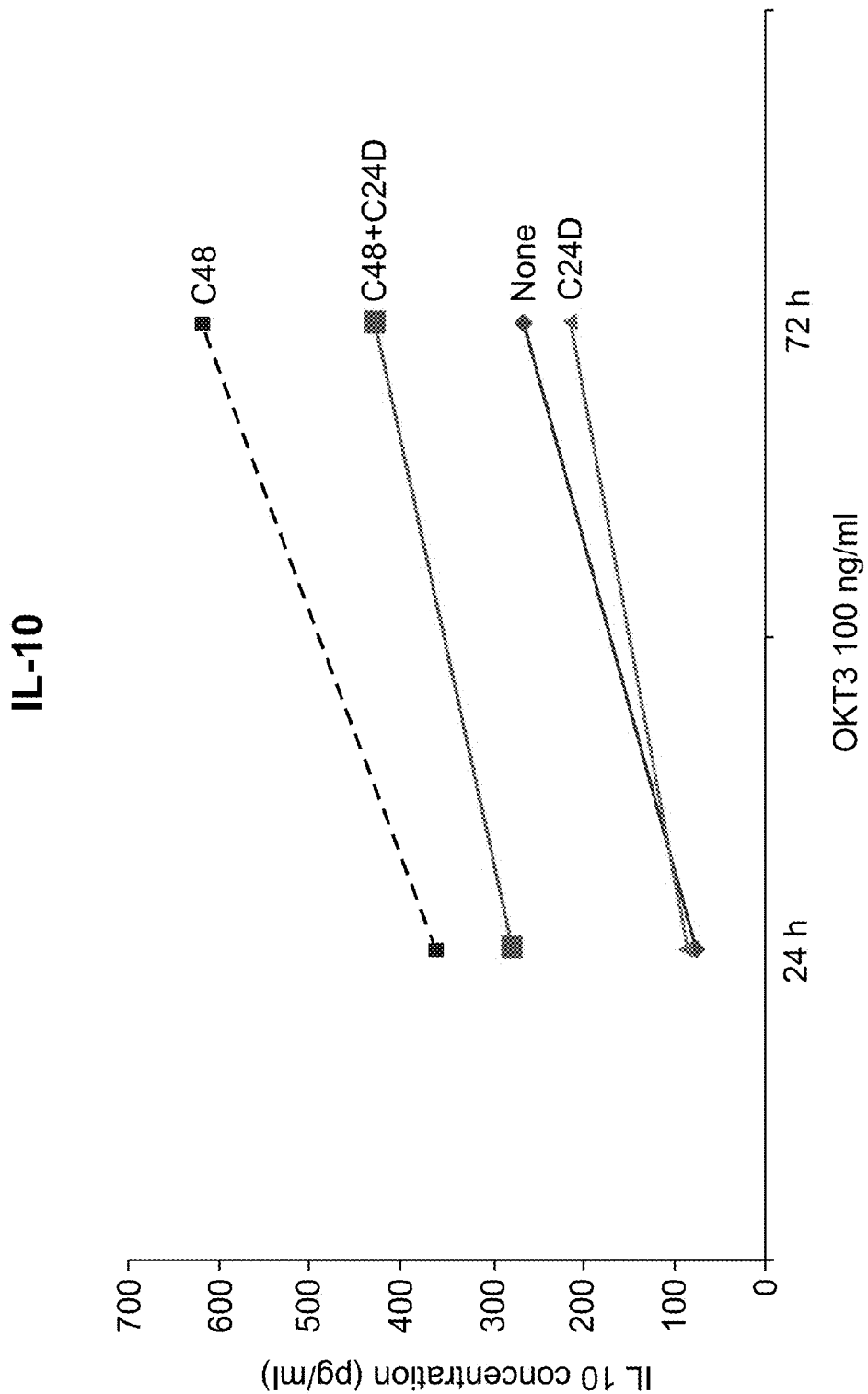

FIG. 10 is a graph illustrating the effect of C24D on IL10 secretion by human PBMCs activated with OKT3 MoAb.

FIGS. 11A-D are photographs illustrating the effect of C24D on human breast cancer cells incubated with human peripheral blood mononuclear cells (PBMC) for 8 days.

FIGS. 12A-B are photographs illustrating the effect of C24D on cell lysis of human breast cancer cells (MCF7) incubated with peripheral blood mononuclear cells (PBMC) for 5 days.

Figure 13A:
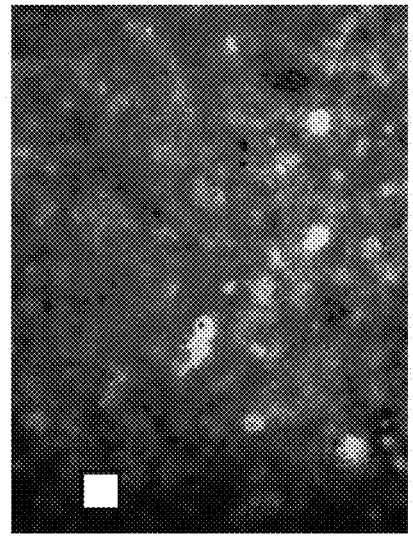
Figure 13B:
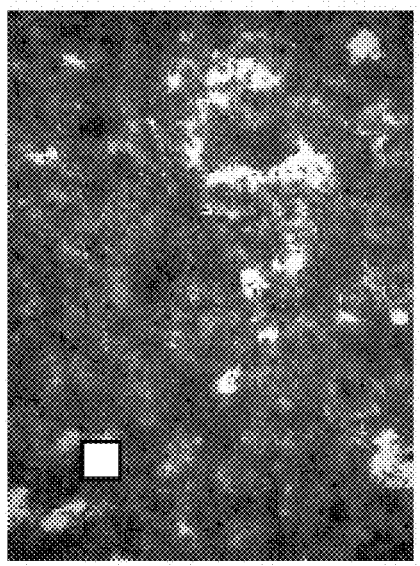
Figure 13C:
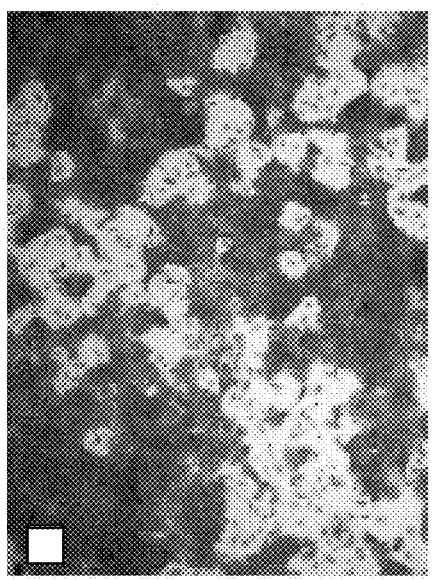

FIGS. 13A-C are photographs illustrating the cytotoxicity of PBMC transferred from MCF7 cultures treated with C24D and control to untreated MCF7 cell secondary cultures.

FIGS. 14A-D are photographs of MCF7 human breast cancer cells grown 19 days in immune-compromised nude mice, treated (18 days i.p.) with C24D (C and D) or PBS (A and B).

Figure 15:
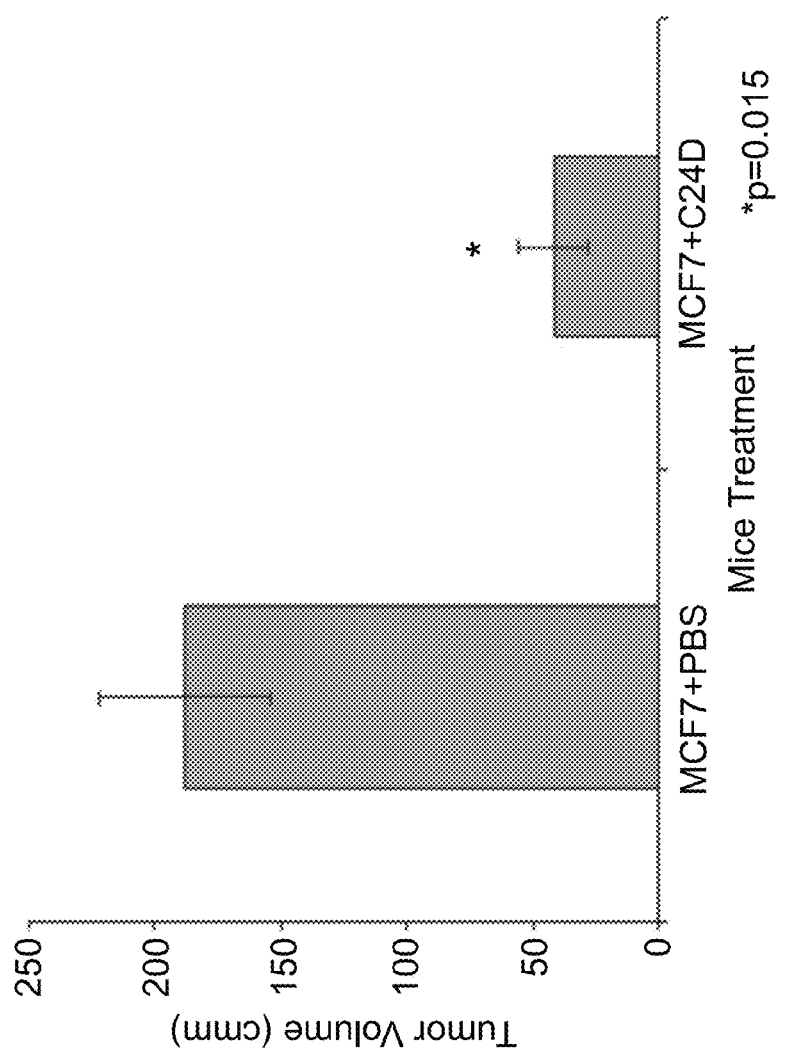

FIG. 15 is a bar graph illustrating the effect of C24D treatment on MCF7 tumor growth in immune-compromised nude mice.

Figure 16A:
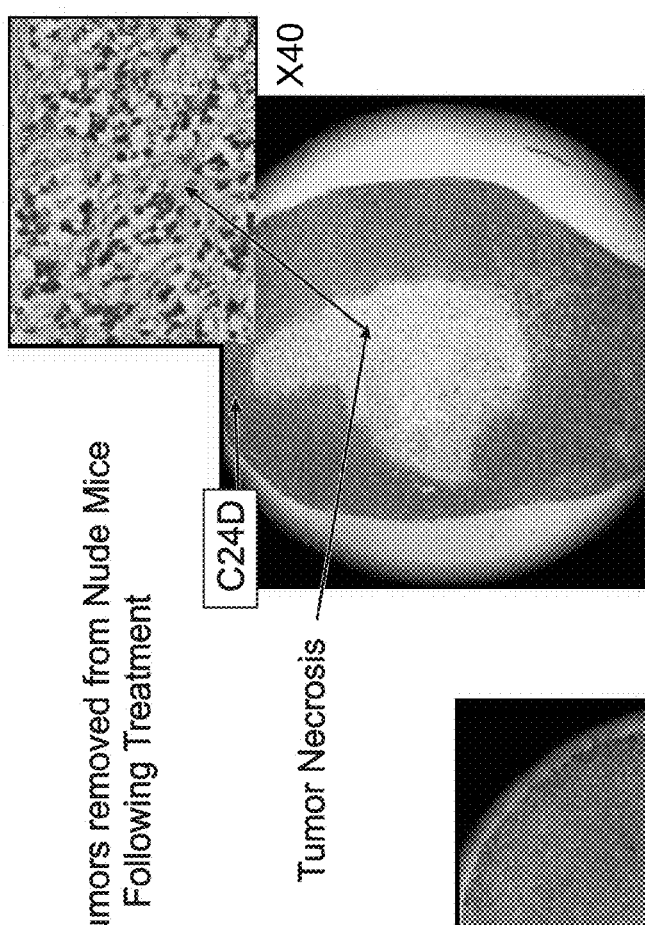
Figure 16B:
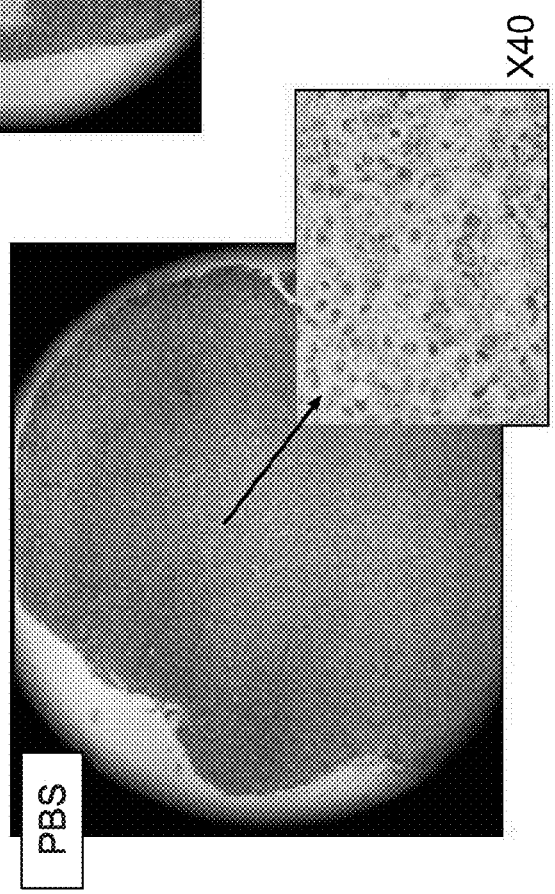

FIGS. 16A-B are photographs comparing the effect of C24D (FIG. 16A) treatment with PBS treatment (FIG. 16B) on tumor necrosis of MCF7 cells grown in immune-compromised nude mice.

FIGS. 17A-C are photographs of T47D cells illustrating the cytotoxic effect of C24D in the presence of PBMCs after 5 days of culture.

Figure 18B:
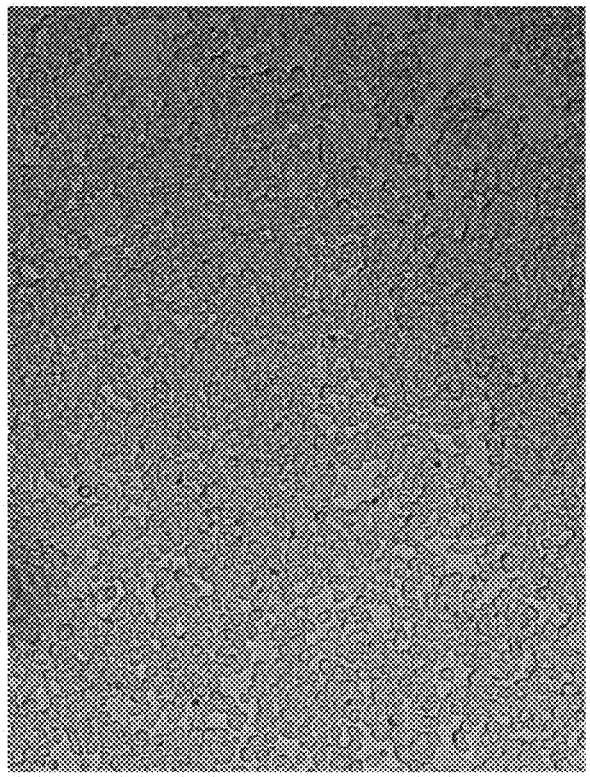
Figure 18A:
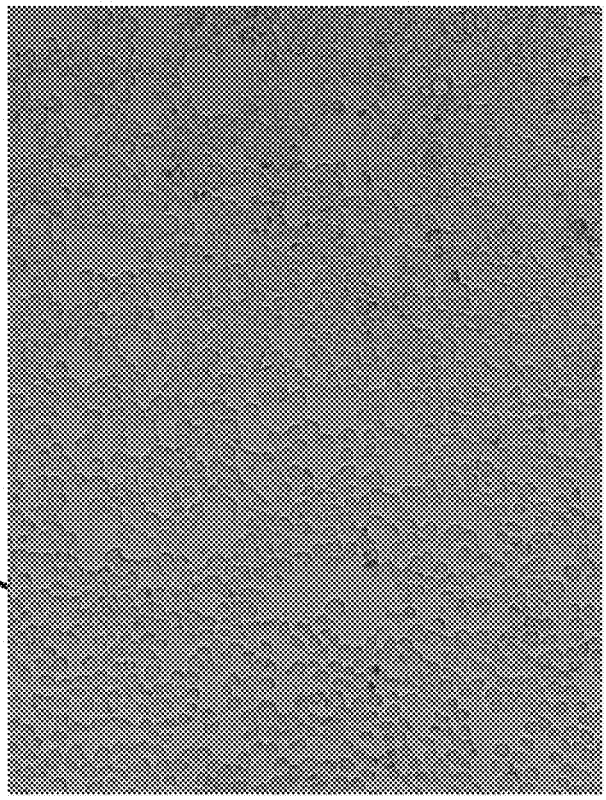
Figure 18C:

FIGS. 18A-C are photographs of T47D cells illustrating the cytotoxic effect of C24D in the presence of PBMCs after 7 days of culture.

Figure 19B:
Figure 19A:
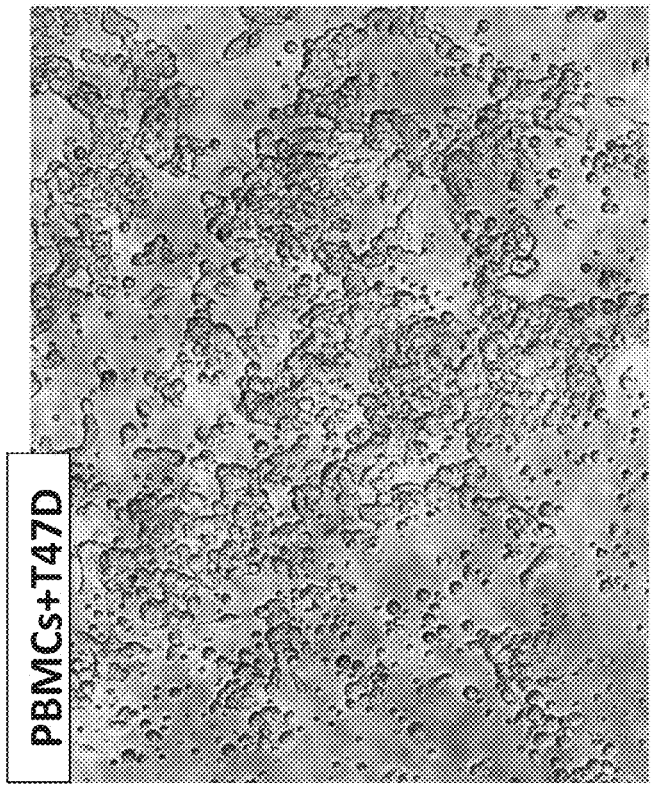
Figure 19C:
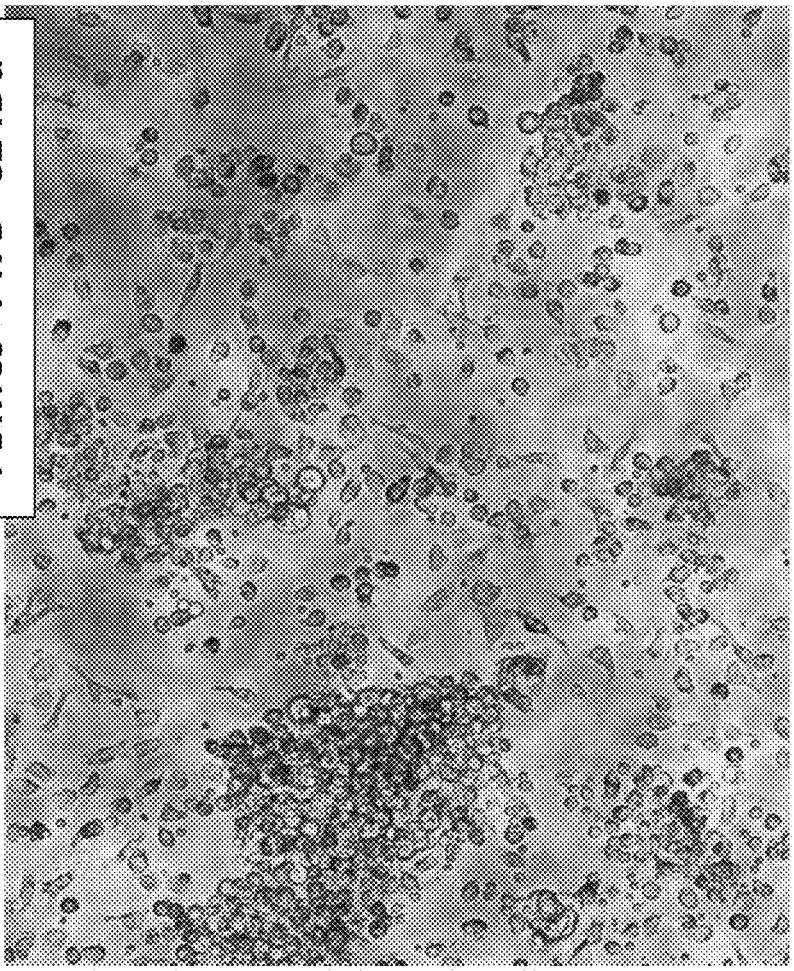

FIGS. 19A-C are photographs illustrating the cytotoxicity of PBMC transferred from T47D cultures treated with C24D for five days and control to untreated T47D cell secondary cultures.

Figure 20B:
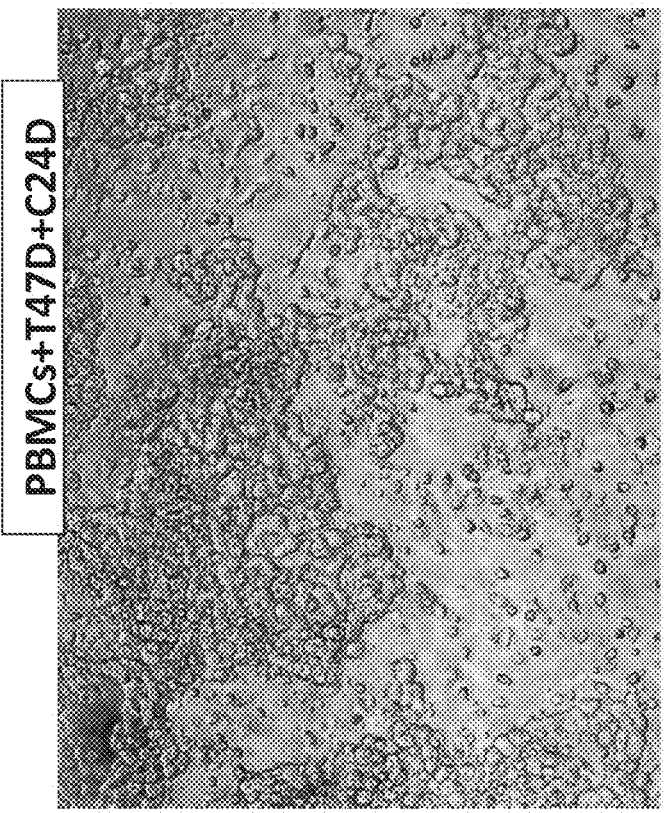
Figure 20A:
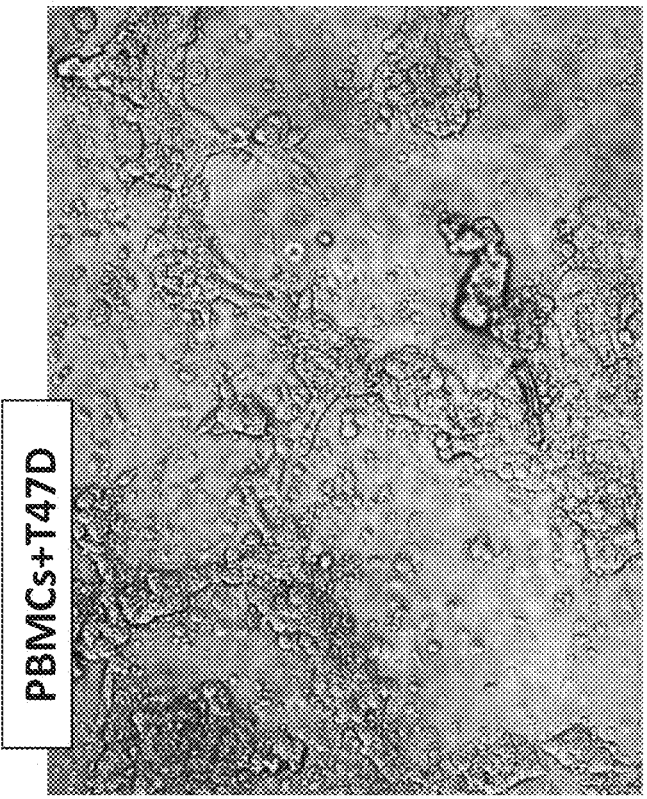

FIGS. 20A-B are photographs illustrating the cytotoxicity of PBMC transferred from T47D cultures treated with C24D for seven days and control to untreated T47D cell secondary cultures.

DESCRIPTION OF SPECIFIC EMBODIMENTS OF THE INVENTION

The present invention, in some embodiments thereof, relates to a multimeric peptide and, more particularly, but not exclusively, to a dimer comprising a Placental Immunoregulatory Ferritin (PLIF) amino acid sequence which is useful for the treatment of cancer.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Placental Immunoregulatory Ferritin (PLIF) is a human pregnancy-related immunomodulator. Recombinant cloned PLIF and its subcloned bioactive domain—C48 are immunosuppressive, which may be partially attributed to the induction of rapid and pronounced IL-10 production by immune cells. PLIF is expressed in the placenta and in human breast cancer tissues, suppressing the host immune response. Further evidence showed that in pregnant mice, blocking PLIF by anti-C48 antibodies inhibited placenta and fetal growth, accompanied by modulation of the cytokine network from Th2 type (IL-10) to a vigorous Th1 type response [IL-2, interferon-γ (INF-γ), TNF]. Moreover, blocking PLIF by anti-C48 antibody treatment inhibited the growth of MCF-7 human breast cancer engrafted into Nude mice infused with human lymphocytes.

The present inventors have now designed and synthesized a novel, synthetic peptide. This novel polypeptide comprised the partial amino acid sequence of the C-terminal part of C48 followed by the addition of Glycine and Cysteine to the N-terminus, and subsequent covalent dimerization (C24D). The C24D molecular weight (M.W.) is 6482, Purity ≥95% (see FIG. 3).

In vitro studies revealed that C24D binds to the surface of human T cells (HDMAR cell line), as illustrated in FIGS. 7A-B and inhibits the binding of C48 to T cells (HDMAR), as illustrated in FIGS. 8A-B. Incubation of activated human peripheral blood mononuclear cells (PBMC) with C24D induces a TH1 type response, i.e., high levels of INF-γ, but not IL-10, as illustrated in FIG. 9. This was measured also in the presence of C48, which otherwise induces a TH2 type response, i.e., high IL-10 levels and no INF-γ (FIG. 10).

The C24D effect on anti-cancer immune activation was exhibited in vitro. This was indicated by the cytotoxic effect and tumor cell growth inhibition of MCF-7 human breast cancer cells cultured with human PBMC for 5-8 days (FIGS. 11A-D, 12A-B and 13A-C). No such effects were exhibited in control cultures treated with phosphate buffer saline (PBS) only. Furthermore, C24D treatment of Nude mice transfused with human lymphocytes and engrafted with MCF-7 tumor cells was associated with tumor growth inhibition and cytotoxicity. This was in contrast to findings in control (PBS) treated mice (FIGS. 14-16).

It may be concluded that treatment of breast cancer patients with C24D polypeptide, a PLIF antagonist, may break the PLIF-induced tolerance to human cancer antigens (breast, lymphoma, leukemia) resulting in cancer immunotherapy and long term anti-cancer immunity.

Thus, according to one aspect of the present invention there is provided a multimeric peptide comprising at least two peptide monomers linked to one another, each of said at least two peptide monomers comprising at least 6 consecutive amino acids from the amino acid sequence as set forth in SEQ ID NO: 1, wherein said at least two peptide monomers are each no longer than 30 amino acids, wherein the multimeric peptide is capable of reducing binding of Placenta Immunomodulatory Factor (PLIF) to human leukocytes.

The phrase "multimeric peptide" as used herein, describes a peptide formed from two or more peptide monomers (i.e. two or more peptide chains) that are associated covalently or non-covalently, with or without linkers. It will be appreciated that the peptide monomers are not linked together so as to form an amide bond through the amine group of one monomer and the carboxylic acid group of the other monomer so as to form a single extended chain.

According to a particular embodiment, the multimeric peptide is a dimer (i.e. comprises two peptide monomers that are associated covalently or non-covalently, with or without linkers). According to a particular embodiment, the two peptide monomers are not linked via a peptide bond.

The multimeric peptides disclosed herein are capable of blocking binding of PLIF to its receptor on white blood cells, thereby acting as an antagonist to the endogenous activity of PLIF.

Methods of ascertaining whether the peptides are capable of antagonizing PLIF are known in the art and include for example analyzing the amount of each peptide that is capable of binding to white blood cells (leukocytes) both separately and/or in the same culture.

The leukocytes are typically human and may be from any source e.g. comprised in T cell lines, peripheral blood mononuclear cells (PBMCs) derived from a subject or macrophages derived from a subject.

Exemplary human T cell lines that may be analyzed include human T cell lines such as HDMAR, Jurkat, CCRF-CEM (ATCC CCL-119).

PBMCs may be prepared as follows: Buffy coats from blood bank donors are layered onto Lymphoprep solution (Nycomed, Oslo, Norway) and spun at 2000 rpm for about 20 minutes. The interface layer is collected, washed, counted, and resuspended in PBS; pH 7.4 to the desired cell concentration.

Binding affinity can be measured by any assay known or available to those skilled in the art, including but not limited to BIAcore measurements, ELISA assays, competition assays, etc. Bioactivity can be measured in vivo or in vitro by any assay known or available to those skilled in the art.

According to one embodiment, binding is measured using an antibody which is capable of specifically recognizing the peptides disclosed herein (i.e. binds with a higher affinity to the multimeric peptides disclosed herein than for C48 (SEQ ID NO: 100) or PLIF under identical conditions). Such antibodies are further described herein below.

The multimeric peptides of this aspect of the present invention typically comprise additional functions such as being capable of increasing interferon gamma (INF-γ) secretion and/or interleukin-10 (IL-10) secretion from activated leukocytes.

According to one embodiment, secretion of INF-γ is increased by at least two fold, or more preferably by at least five fold the amount of INF-γ that is basally secreted from activated leukocytes (i.e. in the absence of the disclosed peptides).

Activation of leukocytes may be effected using any mitogenic agent such as OKT3 MoAb (an antibody which recognizes CD3) or with PLIF or C48 peptide (SEQ ID NO:100). Other methods of activating leukocytes include, but are not limited to activation by lectins (PHA), or activation by cellular antigens in a Mixed Lymphocyte Reaction (MLR) assay.

Methods of analyzing INF-γ secretion include but are not limited to ELISA kits such as those available from DPC, and R&D Systems, USA.

In some embodiments, the multimeric peptide is such that the amino acid sequence of each of its monomers are the same, thus forming a homomultimeric peptide. When the multimeric peptide is a dimer and the two monomers are identical, a homodimeric peptide is formed.

In some embodiments, the multimeric peptide is such that the amino acid sequence of at least two of its peptide monomers are different, thus forming a heteromultimeric peptide. When the multimeric peptide is a dimer and the two monomers are different, a heterodimeric peptide is formed.

As mentioned, the monomers of the multimeric peptide of this aspect of the present invention are derived from the C terminal amino acids of Placenta Immunomodulatory Factor (PLIF) and include at least 6 consecutive amino acids from the sequence as set forth in SEQ ID NO: 1 (His-His-Leu-Leu-Arg-Pro-Arg-Arg-Arg-Lys-Arg-Pro-His-Ser-Ile-Pro-Thr-Pro-Ile-Leu-Ile-Phe-Arg-Ser-Pro).

According to some embodiments, each monomer of the multimeric peptide comprises at least 7 consecutive amino acids from the sequence as set forth in SEQ ID NO: 1.

According to some embodiments, each monomer of the multimeric peptide comprises at least 8 consecutive amino acids from the sequence as set forth in SEQ ID NO: 1.

According to some embodiments, each monomer of the multimeric peptide comprises at least 9 consecutive amino acids from the sequence as set forth in SEQ ID NO: 1.

According to some embodiments, each monomer of the multimeric peptide comprises at least 10 consecutive amino acids from the sequence as set forth in SEQ ID NO: 1.

According to some embodiments, each monomer of the multimeric peptide comprises at least 11 consecutive amino acids from the sequence as set forth in SEQ ID NO: 1.

According to some embodiments, each monomer of the multimeric peptide comprises at least 12 consecutive amino acids from the sequence as set forth in SEQ ID NO: 1.

According to some embodiments, each monomer of the multimeric peptide comprises at least 13 consecutive amino acids from the sequence as set forth in SEQ ID NO: 1.

According to some embodiments, each monomer of the multimeric peptide comprises at least 14 consecutive amino acids from the sequence as set forth in SEQ ID NO: 1.

According to some embodiments, each monomer of the multimeric peptide comprises at least 15 consecutive amino acids from the sequence as set forth in SEQ ID NO: 1.

According to some embodiments, each monomer of the multimeric peptide comprises at least 16 consecutive amino acids from the sequence as set forth in SEQ ID NO: 1.

According to some embodiments, each monomer of the multimeric peptide comprises at least 17 consecutive amino acids from the sequence as set forth in SEQ ID NO: 1.

According to some embodiments, each monomer of the multimeric peptide comprises at least 18 consecutive amino acids from the sequence as set forth in SEQ ID NO: 1.

According to some embodiments, each monomer of the multimeric peptide comprises at least 19 consecutive amino acids from the sequence as set forth in SEQ ID NO: 1.

According to some embodiments, each monomer of the multimeric peptide comprises at least 20 consecutive amino acids from the sequence as set forth in SEQ ID NO: 1.

According to some embodiments, each monomer of the multimeric peptide comprises at least 21 consecutive amino acids from the sequence as set forth in SEQ ID NO: 1.

According to some embodiments, each monomer of the multimeric peptide comprises at least 22 consecutive amino acids from the sequence as set forth in SEQ ID NO: 1.

According to some embodiments, each monomer of the multimeric peptide comprises at least 23 consecutive amino acids from the sequence as set forth in SEQ ID NO: 1.

According to some embodiments, each monomer of the multimeric peptide comprises the full length sequence as set forth in SEQ ID NO: 1.

The term "C24D" as used herein, refers to a dimer of a peptide from PLIF having the sequence as set forth in SEQ ID NO: 1 and two linking amino acids.

According to further embodiments, each monomer of the multimeric peptide comprises the sequence as set forth in SEQ ID NO: 101—Cys-Gly-His-His-Leu-Leu-Arg-Pro-Arg-Arg-Arg-Lys-Arg-Pro-His-Ser-Ile-Pro-Thr-Pro-Ile-Leu-Ile-Phe-Arg-Ser-Pro.

According to a particular embodiment the amino acid sequence derived from SEQ ID NO: 1 is HSIPTPILIFRSP (SEQ ID NO: 2), HLLRPRRRKRPHSI (SEQ ID NO: 3), RPRRRKRPHSIP (SEQ ID NO: 4), SIPTPILIFRSP (SEQ ID NO: 5), PHSIPTPILIFRSP (SEQ ID NO: 6) or HHLLR-PRRRKR (SEQ ID NO: 7).

Preferably, each monomer of the multimeric peptide comprises at least 6, at least 7, at least 8, at least 9, at least 10, at least 11, at least 12, at least 13, at least 14 consecutive amino acids from the sequence as set forth in SEQ ID NO: 14—RPHSIPTPILIFRSP.

Additional contemplated peptides which are comprised in the monomers of the multimeric peptide include those set forth in Table 1, herein below.

TABLE 1

| Sequence | SEQ ID |
|---|---|
| His-His-Leu-Leu-Arg-Pro | 15 |
| His-Leu-Leu-Arg-Pro-Arg | 16 |
| Leu-Leu-Arg-Pro-Arg-Arg | 17 |
| Leu-Arg-Pro-Arg-Arg-Lys | 18 |
| Arg-Pro-Arg-Arg-Lys-Arg | 19 |
| Pro-Arg-Arg-Lys-Arg-Pro | 20 |
| Arg-Arg-Lys-Arg-Pro-His | 21 |
| Arg-Lys-Arg-Pro-His-Ser | 22 |
| Lys-Arg-Pro-His-Ser-Ile | 23 |
| Arg-Pro-His-Ser-Ile-Pro | 24 |
| Pro-His-Ser-Ile-Pro-Thr | 25 |
| His-Ser-Ile-Pro-Thr-Pro | 26 |
| Ser-Ile-Pro-Thr-Pro-Ile | 27 |
| Ile-Pro-Thr-Pro-Ile-Leu | 28 |
| Pro-Thr-Pro-Ile-Leu-Ile | 29 |
| Thr-Pro-Ile-Leu-Ile-Phe | 30 |
| Pro-Ile-Leu-Ile-Phe-Arg | 31 |
| Ile-Leu-Ile-Phe-Arg-Ser | 32 |
| Leu-Ile-Phe-Arg-Ser-Pro | 33 |
| His-His-Leu-Leu-Arg-Pro-Arg | 34 |
| His-Leu-Leu-Arg-Pro-Arg-Arg | 35 |
| Leu-Leu-Arg-Pro-Arg-Arg-Lys | 36 |
| Leu-Arg-Pro-Arg-Arg-Lys-Arg | 37 |
| Arg-Pro-Arg-Arg-Lys-Arg-Pro | 38 |
| Pro-Arg-Arg-Lys-Arg-Pro-His | 39 |
| Arg-Arg-Lys-Arg-Pro-His-Ser | 40 |
| Arg-Lys-Arg-Pro-His-Ser-Ile | 41 |
| Lys-Arg-Pro-His-Ser-Ile-Pro | 42 |
| Arg-Pro-His-Ser-Ile-Pro-Thr | 43 |
| Pro-His-Ser-Ile-Pro-Thr-Pro | 44 |
| His-Ser-Ile-Pro-Thr-Pro-Ile | 45 |
| Ser-Ile-Pro-Thr-Pro-Ile-Leu | 46 |
| Ile-Pro-Thr-Pro-Ile-Leu-Ile | 47 |
| Pro-Thr-Pro-Ile-Leu-Ile-Phe | 48 |
| Thr-Pro-Ile-Leu-Ile-Phe-Arg | 49 |
| Pro-Ile-Leu-Ile-Phe-Arg-Ser | 50 |
| Ile-Leu-Ile-Phe-Arg-Ser-Pro | 51 |
| His-His-Leu-Leu-Arg-Pro-Arg-Arg | 52 |
| His-Leu-Leu-Arg-Pro-Arg-Arg-Lys | 53 |
| Leu-Leu-Arg-Pro-Arg-Arg-Lys-Arg | 54 |
| Leu-Arg-Pro-Arg-Arg-Lys-Arg-Pro | 55 |
| Arg-Pro-Arg-Arg-Lys-Arg-Pro-His | 56 |
| Pro-Arg-Arg-Lys-Arg-Pro-His-Ser | 57 |
| Arg-Arg-Lys-Arg-Pro-His-Ser-Ile | 58 |
| Arg-Lys-Arg-Pro-His-Ser-Ile-Pro | 59 |
| Lys-Arg-Pro-His-Ser-Ile-Pro-Thr | 60 |
| Arg-Pro-His-Ser-Ile-Pro-Thr-Pro | 61 |
| Pro-His-Ser-Ile-Pro-Thr-Pro-Ile | 62 |
| His-Ser-Ile-Pro-Thr-Pro-Ile-Leu | 63 |
| Ser-Ile-Pro-Thr-Pro-Ile-Leu-Ile | 64 |
| Ile-Pro-Thr-Pro-Ile-Leu-Ile-Phe | 65 |
| Pro-Thr-Pro-Ile-Leu-Ile-Phe-Arg | 66 |
| Thr-Pro-Ile-Leu-Ile-Phe-Arg-Ser | 67 |
| Pro-Ile-Leu-Ile-Phe-Arg-Ser-Pro | 68 |
| His-His-Leu-Leu-Arg-Pro-Arg-Arg-Lys | 69 |
| His-Leu-Leu-Arg-Pro-Arg-Arg-Lys-Arg | 70 |
| Leu-Leu-Arg-Pro-Arg-Arg-Lys-Arg-Pro | 71 |
| Leu-Arg-Pro-Arg-Arg-Lys-Arg-Pro-His | 72 |
| Arg-Pro-Arg-Arg-Lys-Arg-Pro-His-Ser | 73 |
| Pro-Arg-Arg-Lys-Arg-Pro-His-Ser-Ile | 74 |
| Arg-Arg-Lys-Arg-Pro-His-Ser-Ile-Pro | 75 |
| Arg-Lys-Arg-Pro-His-Ser-Ile-Pro-Thr | 76 |
| Lys-Arg-Pro-His-Ser-Ile-Pro-Thr-Pro | 77 |
| Arg-Pro-His-Ser-Ile-Pro-Thr-Pro-Ile | 78 |
| Pro-His-Ser-Ile-Pro-Thr-Pro-Ile-Leu | 79 |
| His-Ser-Ile-Pro-Thr-Pro-Ile-Leu-Ile | 80 |
| Ser-Ile-Pro-Thr-Pro-Ile-Leu-Ile-Phe | 81 |
| Ile-Pro-Thr-Pro-Ile-Leu-Ile-Phe-Arg | 82 |
| Pro-Thr-Pro-Ile-Leu-Ile-Phe-Arg-Ser | 83 |
| Thr-Pro-Ile-Leu-Ile-Phe-Arg-Ser-Pro | 84 |
| His-His-Leu-Leu-Arg-Pro-Arg-Arg-Lys-Arg | 85 |
| His-Leu-Leu-Arg-Pro-Arg-Arg-Lys-Arg-Pro | 86 |
| Leu-Leu-Arg-Pro-Arg-Arg-Lys-Arg-Pro-His | 87 |
| Leu-Arg-Pro-Arg-Arg-Lys-Arg-Pro-His-Ser | 88 |
| Arg-Pro-Arg-Arg-Lys-Arg-Pro-His-Ser-Ile | 89 |
| Pro-Arg-Arg-Lys-Arg-Pro-His-Ser-Ile-Pro | 90 |

TABLE 1-continued

| Sequence | SEQ ID |
|---|---|
| Arg-Arg-Lys-Arg-Pro-His-Ser-Ile-Pro-Thr | 91 |
| Arg-Lys-Arg-Pro-His-Ser-Ile-Pro-Thr-Pro | 92 |
| Lys-Arg-Pro-His-Ser-Ile-Pro-Thr-Pro-Ile | 93 |
| Arg-Pro-His-Ser-Ile-Pro-Thr-Pro-Ile-Leu | 94 |
| Pro-His-Ser-Ile-Pro-Thr-Pro-Ile-Leu-Ile | 95 |
| His-Ser-Ile-Pro-Thr-Pro-Ile-Leu-Ile-Phe | 96 |
| Ser-Ile-Pro-Thr-Pro-Ile-Leu-Ile-Phe-Arg | 97 |
| Ile-Pro-Thr-Pro-Ile-Leu-Ile-Phe-Arg-Ser | 98 |
| Pro-Thr-Pro-Ile-Leu-Ile-Phe-Arg-Ser-Pro | 99 |

The term "peptide" as used herein refers to a polymer of natural or synthetic amino acids, encompassing native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides even more stable while in a body or more capable of penetrating into cells.

Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as Phenylglycine, TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids (stereoisomers).

Tables 2 and 3 below list naturally occurring amino acids (Table 2) and non-conventional or modified amino acids (Table 3) which can be used with the present invention.

TABLE 2

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 3

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |

TABLE 3-continued

| Non-conventional amino acid | Code | Non-conventional amino acid | Code |
|---|---|---|---|
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α ethylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α thylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |

TABLE 3-continued

| Non-conventional amino acid | Code | Non-conventional amino acid | Code |
|---|---|---|---|
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α ethylhistidine | Mhis | L-α-methylhomophenylalanine | Mhphe |
| L-α thylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α ethylvaline | Mtrp | L-α-methyltyrosine | Mtyr |
| L-α-methylleucine | Mval | L-N-methylhomophenylalanine | Nmhphe |
|  | Nnbhm |  |  |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc |  |  |

It will be appreciated that additional peptides are contemplated by the present invention as well as those disclosed herein, which may be synthesized (comprising conservative or non-conservative substitutions) in order to "tweak the system" and generate PLIF-derived peptides with improved characteristics i.e. comprising an enhanced ability to block PLIF binding and/or to stimulate the secretion of IFN from T lymphocytes.

Thus, in other embodiments, the peptide monomers comprise a homolog, a variant, or a functional fragment of the sequences described herein above. In another embodiment, the peptide monomers comprise an amino acid sequence that is about 60%, 65%, 70%, 75%, 80%, 85%, 90%, or 95% identical to the sequences described herein above.

The present teachings further contemplate cyclic peptides or cyclic structures within the peptides. Methods of cyclization are well known in the art, see for instance in WO2010/041237, which is hereby incorporated by reference.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cyclohexylmethyl glycine for alanine, isoleucine for glycine, or —NH—CH[(—$CH_2$)$_5$—COOH]—CO— for aspartic acid. Those non-conservative substitutions which fall under the scope of the present invention are those which still constitute a peptide having anti-bacterial properties.

The N and C termini of the peptides of the present invention may be protected by function groups. Suitable functional groups are described in Green and Wuts, "Protecting Groups in Organic Synthesis", John Wiley and Sons, Chapters 5 and 7, 1991, the teachings of which are incorporated herein by reference.

Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a peptide of the present invention is protected, preferably with a methyl, ethyl, benzyl or substituted benzyl ester.

Examples of N-terminal protecting groups include acyl groups (—CO—R1) and alkoxy carbonyl or aryloxy carbonyl groups (—CO—O—R1), wherein R1 is an aliphatic, substituted aliphatic, benzyl, substituted benzyl, aromatic or a substituted aromatic group. Specific examples of acyl groups include acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include CH3-O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—. Adamantan, naphtalen, myristoleyl, tuluen, biphenyl, cinnamoyl, nitrobenzoy, toluoyl, furoyl, benzoyl, cyclohexane, norbornane, Z-caproic. In order to facilitate the N-acylation, one to four glycine residues can be present in the N-terminus of the molecule.

The carboxyl group at the C-terminus of the compound can be protected, for example, by an amide (i.e., the hydroxyl group at the C-terminus is replaced with —NH$_2$, —NHR$_2$ and —NR$_2$R$_3$) or ester (i.e. the hydroxyl group at the C-terminus is replaced with —OR$_2$). R$_2$ and R$_3$ are independently an aliphatic, substituted aliphatic, benzyl, substituted benzyl, aryl or a substituted aryl group. In addition, taken together with the nitrogen atom, R$_2$ and R$_3$ can form a C4 to C8 heterocyclic ring with from about 0-2 additional heteroatoms such as nitrogen, oxygen or sulfur. Examples of suitable heterocyclic rings include piperidinyl, pyrrolidinyl, morpholino, thiomorpholino or piperazinyl. Examples of C-terminal protecting groups include —NH$_2$, —NHCH$_3$, —N(CH$_3$)$_2$, —NH(ethyl), —N(ethyl)$_2$, —N(methyl) (ethyl), —NH(benzyl), —N(C1-C4 alkyl)(benzyl), —NH(phenyl), —N(C1-C4 alkyl) (phenyl), —OCH$_3$, —O-(ethyl), —O-(n-propyl), —O-(n-butyl), —O-(iso-propyl), —O-(sec-butyl), —O-(t-butyl), —O-benzyl and —O-phenyl.

The peptides of the present invention may also comprise non-amino acid moieties, such as for example, hydrophobic moieties (various linear, branched, cyclic, polycyclic or heterocyclic hydrocarbons and hydrocarbon derivatives) attached to the peptides; various protecting groups, especially where the compound is linear, which are attached to the compound's terminals to decrease degradation. Chemical (non-amino acid) groups present in the compound may be included in order to improve various physiological properties such; decreased degradation or clearance; decreased repulsion by various cellular pumps, improve immunogenic activities, improve various modes of administration (such as attachment of various sequences which allow penetration through various barriers, through the gut, etc.); increased specificity, increased affinity, decreased toxicity and the like.

Exemplary side chain protecting groups and their positioning are described in the Examples section herein below.

Linking of the monomers of the PLIF derived monomers may be effected using any method known in the art provided that the linking does not substantially interfere with the bioactivity of the multimeric peptide—e.g. to interfere with the ability of the multimeric peptide to block the binding of PLIF to receptors on leukocytes (e.g. T cells).

The monomers of this aspect of the present invention may be linked through a linking moiety.

Examples of linking moieties include but are not limited to a simple covalent bond, a flexible peptide linker, a disulfide bridge or a polymer such as polyethylene glycol (PEG). Peptide linkers may be entirely artificial (e.g., comprising 2 to 20 amino acid residues independently selected from the group consisting of glycine, serine, asparagine, threonine and alanine) or adopted from naturally occurring proteins. Disulfide bridge formation can be achieved, e.g., by addition of cysteine residues, as further described herein below. Linking through polyethylene glycols (PEG) can be achieved by reaction of monomers having free cysteines with multifunctional PEGs, such as linear bis-maleimide PEGs. Alternatively, linking can be performed though the glycans on the monomer after their oxidation to aldehyde form and using multifunctional PEGs containing aldehyde-reactive groups.

Selection of the position of the link between the two monomers should take into account that the link should not substantially interfere with the ability of the multimer to block the binding of PLIF to receptors on T cells.

Thus, for example, the linking moiety is optionally a moiety which is covalently attached to a side chain, an N-terminus or a C-terminus of the first peptide monomer, as well as to a side chain, an N-terminus or a C-terminus of the second peptide monomer.

Preferably the linking moiety is attached to the C-terminus of the first peptide monomer, and to the C-terminus of the second peptide monomer.

As mentioned, the linking moiety used in this aspect of the present invention may be a cysteine residue.

Thus, in some embodiments of the invention, each of the peptide monomers comprises an amino acid sequence as described herein above and further comprise at least one cysteine residue, such that the peptide monomers are covalently linked to one another via a disulfide bridge formed between a cysteine residue in one peptide monomer and a cysteine residue in another peptide monomer.

Typically, the cysteine is situated at the carboxy end of the peptide monomers.

Hereinthroughout, the phrases "disulfide bridge" and "disulfide bond" are used interchangeably, and describe a —S—S— bond.

The linker may comprise additional amino acids linked together by peptide bonds which serve as spacers such that the linker does not interfere with the biological activity of the final compound. The linker is preferably made up of amino acids linked together by peptide bonds. Thus, in preferred embodiments, the linker is made up of from 1 to 10 amino acids linked by peptide bonds, wherein the amino acids are selected from the 20 naturally occurring amino acids. Some of these amino acids may be glycosylated, as is well understood by those in the art. In a more preferred embodiment, besides cysteine the amino acids in the linker are selected from glycine, alanine, proline, asparagine, glutamine, and lysine. Even more preferably, besides cysteine, the linker is made up of a majority of amino acids that are sterically unhindered, such as glycine and alanine.

Thus, according to one embodiment the linker comprises the sequence cysteine-glycine.

Exemplary monomer sequences are thus set forth by the following sequences:

```
                         (SEQ ID NO: 8)
CGHSIPTPILIFRSP, (SEQ ID NO: 9)
CGHLLRPRRRKRPHSI, (SEQ ID NO: 10)
CGRPRRRKRPHSIP, (SEQ ID NO: 11)
CGSIPTPILIFRSP, (SEQ ID NO: 12)
CGPHSIPTPILIFRSP
or (SEQ ID NO: 13)
CGHHLLRPRRRKR.
```

Non-peptide linkers are also possible. For example, alkyl linkers such as —NH—(CH.sub.2).sub.s-C(O)—, wherein s=2-20 could be used. These alkyl linkers may further be substituted by any non-sterically hindering group such as lower alkyl (e.g., $C_1$-$C_6$) lower acyl, halogen (e.g., Cl, Br), CN, $NH_2$, phenyl, etc. An exemplary non-peptide linker is a PEG linker.

Thus, in some embodiments, at least one of monomers is PEGylated or chemically modified to another form. PEGylation of the molecules can be carried out, e.g., according to the methods described in Youngster et al., Curr Pharm Des (2002), 8:2139; Grace et al., J Interferon Cytokine Res (2001), 21:1103; Pepinsky et al., J Pharmacol Exp Ther (2001), 297:1059; Pettit et al., J Biol Chem (1997), 272:2312; Goodson et al. Biotechnology NY (1990), 8:343; Katre; J Immunol (1990), 144:209, Behrens et al US2006/0198819 A1, Klausen et al US2005/0113565 A1.

Any kind of polyethylene glycol is suitable for the present invention provided that the PEG-polypeptide-oligomer is still capable of antagonizing or neutralizing the binding of PLIF with its receptor which can be assayed according to methods known in the art.

Preferably, the polyethylene glycol of the polypeptide-dimer of the present invention is PEG 1000, 2000, 3000, 5000, 10000, 15000, 20000 or 40000 with PEG 20000 or 40000 being particularly preferred.

According to another embodiment the link is effected using a coupling agent.

The term "coupling agent", as used herein, refers to a reagent that can catalyze or form a bond between two or more functional groups intra-molecularly, inter-molecularly or both. Coupling agents are widely used to increase polymeric networks and promote crosslinking between polymeric chains, hence, in the context of some embodiments of the present invention, the coupling agent is such that can promote crosslinking between polymeric chains; or such that can promote crosslinking between amino functional groups and carboxylic functional groups, or between other chemically compatible functional groups of polymeric chains. In some embodiments of the present invention the term "coupling agent" may be replaced with the term "crosslinking agent". In some embodiments, one of the polymers serves as the coupling agent and acts as a crosslinking polymer.

By "chemically compatible" it is meant that two or more types of functional groups can react with one another so as to form a bond.

Exemplary functional groups which are typically present in gelatins and alginates include, but are not limited to, amines (mostly primary amines —$NH_2$), carboxyls (—$CO_2H$), sulfhydryls and hydroxyls (—SH and —OH respectively), and carbonyls (—COH aldehydes and —CO— ketones).

Primary amines occur at the N-terminus of polypeptide chains (called the alpha-amine), at the side chain of lysine (Lys, K) residues (the epsilon-amine), as found in gelatin, as well as in various naturally occurring polysaccharides and aminoglycosides. Because of its positive charge at physiologic conditions, primary amines are usually outward-facing (i.e., found on the outer surface) of proteins and other macromolecules; thus, they are usually accessible for conjugation.

Carboxyls occur at the C-terminus of polypeptide chain, at the side chains of aspartic acid (Asp, D) and glutamic acid (Glu, E), as well as in naturally occurring aminoglycosides and polysaccharides such as alginate. Like primary amines, carboxyls are usually on the surface of large polymeric compounds such as proteins and polysaccharides.

Sulfhydryls and hydroxyls occur in the side chain of cysteine (Cys, C) and serine, (Ser, S) respectively. Hydroxyls are abundant in polysaccharides and aminoglycosides.

Carbonyls as ketones or aldehydes can be form in glycoproteins, glycosides and polysaccharides by various oxidizing processes, synthetic and/or natural.

According to some embodiments of the present invention, the coupling agent can be selected according to the type of functional groups and the nature of the crosslinking bond that can be formed therebetween. For example, carboxyl coupling directly to an amine can be afforded using a carbodiimide type coupling agent, such as EDC; amines may be coupled to carboxyls, carbonyls and other reactive functional groups by N-hydroxysuccinimide esters (NHS-esters), imidoester, PFP-ester or hydroxymethyl phosphine; sulfhydryls may be coupled to carboxyls, carbonyls, amines and other reactive functional groups by maleimide, haloacetyl (bromo- or iodo-), pyridyldisulfide and vinyl sulfone; aldehydes as in oxidized carbohydrates, may be coupled to other reactive functional groups with hydrazide; and hydroxyl may be coupled to carboxyls, carbonyls, amines and other reactive functional groups with isocyanate.

Hence, suitable coupling agents that can be used in some embodiments of the present invention include, but are not limited to, carbodiimides, NHS-esters, imidoesters, PFP-esters or hydroxymethyl phosphines.

The peptides of the present invention can be biochemically synthesized such as by using standard solid phase techniques. These methods include exclusive solid phase synthesis, partial solid phase synthesis methods, fragment condensation, classical solution synthesis. Solid phase polypeptide synthesis procedures are well known in the art and further described by John Morrow Stewart and Janis Dillaha Young, Solid Phase Polypeptide Syntheses (2nd Ed., Pierce Chemical Company, 1984).

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

Recombinant techniques may also be used to generate the monomers of the present invention. To produce a peptide of the present invention using recombinant technology, a polynucleotide encoding the monomer of the present invention is ligated into a nucleic acid expression vector, which comprises the polynucleotide sequence under the transcriptional control of a cis-regulatory sequence (e.g., promoter sequence) suitable for directing constitutive, tissue specific or inducible transcription of the monomers of the present invention in the host cells.

In addition to being synthesizable in host cells, the monomers of the present invention can also be synthesized using in vitro expression systems. These methods are well known in the art and the components of the system are commercially available.

Typically, the monomers are synthesized as individual peptides, following which, depending on the linking moiety present in the monomers, linking is effected. For example, if the linking moiety is a cysteine residue, thiol oxidation is performed.

Thus, according to another aspect of the present invention there is provided a method of generating a dimeric peptide, the method comprising linking two isolated peptides, which each of said at least two isolated peptides comprise at least 6 consecutive amino acids and no more than 30 amino acids from the amino acid sequence as set forth in SEQ ID NO: 1.

When Cys residue is used as a linking moiety, disulfide bonds may be formed by oxidation thereof. In one embodiment the control of cysteine bond formation is exercised by choosing an oxidizing agent of the type and concentration effective to optimize formation of the multimer. Examples of oxidizing agent include iodine, dimethylsulfoxide (DMSO), potassium ferricyanide, and the like.

If the monomers comprise two or more cysteine residues, isomers resulting from disulfide bonds of different binding manner may be erroneously obtained. A peptide dimer wherein a disulfide bond is formed between intended cysteine residues can be prepared by selecting a particular combination of protecting groups for cysteine side chains. Examples of the combination of protecting groups include MeBzl (methylbenzyl) and Acm (acetamidemethyl) groups, Trt (trityl) and Acm groups, Npys (3-nitro-2-pyridylthio) and Acm groups, S-Bu-t (S-tert-butyl) and Acm groups, and the like. For example, in the case of a combination of MeBzl and Acm groups, the preparation can be carried out by a method comprising removing protecting groups other than MeBzl group and a protecting group(s) on the cysteine side chain, and subjecting the resulting monomer solution to air-oxidation to form a disulfide bond(s) between the deprotected cysteine residues, followed by deprotection and oxidization with iodine to form a disulfide bond(s) between the cysteine residues previously protected by Acm.

In embodiments where a peptide dimer is dimerized via a linker moiety, said linker may be incorporated into the peptide during peptide synthesis. For example, where a linker moiety contains two functional groups capable of serving as initiation sites for peptide synthesis and a third functional group (e.g., a carboxyl group or an amino group) that enables binding to another molecular moiety, the linker may be conjugated to a solid support. Thereafter, two peptide monomers may be synthesized directly onto the two reactive nitrogen groups of the linker moiety in a variation of the solid phase synthesis technique.

In alternate embodiments where a peptide dimer is dimerized by a linker moiety, said linker may be conjugated to the two peptide monomers of a peptide dimer after peptide synthesis. Such conjugation may be achieved by methods well established in the art. In one embodiment, the linker contains at least two functional groups suitable for attachment to the target functional groups of the synthesized peptide monomers. For example, a linker with two free amine groups may be reacted with the C-terminal carboxyl groups of each of two peptide monomers. In another example, linkers containing two carboxyl groups, either preactivated or in the presence of a suitable coupling reagent, may be reacted with the N-terminal or side chain amine groups, or C-terminal lysine amides, of each of two peptide monomers.

Monomers of the invention can be attached to water-soluble polymers (e.g., PEG) using any of a variety of chemistries to link the water-soluble polymer(s) to the receptor-binding portion of the molecule (e.g., peptide+spacer). A typical embodiment employs a single attachment junction for covalent attachment of the water soluble polymer(s) to the receptor-binding portion, however in alternative embodiments multiple attachment junctions may be used, including further variations wherein different species of water-soluble polymer are attached to the receptor-binding portion at distinct attachment junctions, which may include covalent attachment junction(s) to the spacer and/or to one or both peptide chains. In some embodiments, the dimer or higher order multimer will comprise distinct species of peptide chain (i.e., a heterodimer or other heteromultimer). By way of example and not limitation, a dimer may comprise a first peptide chain having a PEG attachment junction and the second peptide chain may either lack a PEG attachment junction or utilize a different linkage chemistry than the first peptide chain and in some variations the spacer may contain or lack a PEG attachment junction and said spacer, if PEGylated, may utilize a linkage chemistry different than that of the first and/or second peptide chains. An alternative embodiment employs a PEG attached to the spacer portion of the receptor-binding portion and a different water-soluble polymer (e.g., a carbohydrate) conjugated to a side chain of one of the amino acids of the peptide portion of the molecule.

The peptides of the present invention may also comprise non-amino acid moieties, such as for example, hydrophobic moieties (various linear, branched, cyclic, polycyclic or heterocyclic hydrocarbons and hydrocarbon derivatives) attached to the peptides; various protecting groups, especially where the compound is linear, which are attached to the compound's terminals to decrease degradation. Chemical (non-amino acid) groups present in the compound may be included in order to improve various physiological properties such; decreased degradation or clearance; decreased repulsion by various cellular pumps, improve immunogenic activities, improve various modes of administration (such as attachment of various sequences which allow penetration through various barriers, through the gut, etc.); increased specificity, increased affinity, decreased toxicity and the like.

According to one embodiment, the peptides of the present invention are attached to a sustained-release enhancing agent. Exemplary sustained-release enhancing agents include, but are not limited to hyaluronic acid (HA), alginic acid (AA), polyhydroxyethyl methacrylate (Poly-HEMA), polyethylene glycol (PEG), glyme and polyisopropylacrylamide.

Attaching the amino acid sequence component of the peptides of the invention to other non-amino acid agents may be by covalent linking, by non-covalent complexion, for example, by complexion to a hydrophobic polymer, which can be degraded or cleaved producing a compound capable of sustained release; by entrapping the amino acid part of the peptide in liposomes or micelles to produce the final peptide of the invention. The association may be by the entrapment of the amino acid sequence within the other component (liposome, micelle) or the impregnation of the amino acid sequence within a polymer to produce the final peptide of the invention.

Since the multimeric peptides described herein are capable of reducing binding of PLIF to its receptor on leukocytes, the peptides may be used for treating diseases associated with a TH2:TH1 bias (i.e. diseases which are associated with increased tolerance to a foreign antigen). Such diseases are typically associated with T cells secreting a high level of IL-10 and a low level of IL-2, INF-γ) and TNF.

Examples of such diseases include cancer and retrovirally mediated diseases (HIV infection).

The term "cancer" as used herein refers to proliferative diseases including by not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphocytic leukemia, such as Acute lumphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

According to a particular embodiment, the cancer is selected from the group consisting of Hodgkin's lymphoma, non-Hodgkin's lymphoma, acute lymphatic leukemia (ALL) and breast cancer.

Retrovirally mediated diseases include, but are not limited to HIV and cancers such as acute and chronic leukemia.

Treatment of diseases may be effected by administering the multimeric peptide alone, or together with a carrier as a pharmaceutical composition.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent.

Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions.

In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

Determining whether a subject is suitable for the treatment with the multimeric peptide described herein may be carried out by analyzing a level of PLIF in a sample of the subject, wherein expression of PLIF above a predetermined level is indicative that the subject is a suitable candidate for treatment. Typically, the level of PLIF is at least 1.5 the level found in a healthy subject and more preferably at least twice the level found in the healthy subject. The full length sequence of PLIF is provided in U.S. Pat. No. 7,217,686.

According to a particular embodiment, the sample is a blood sample, a serum sample of a lymphocyte sample. According to still another embodiment the sample is a tumor sample (e.g. by removal of the tumor during a biopsy).

Analysis of PLIF levels may be effected on the protein level—e.g. by Western blot analysis, immunohistochemical analysis, FACs sorting or radioimmunoassay.

U.S. Pat. No. 4,882,270, incorporated herein by reference, discloses a method for detecting PLIF, by using antibodies.

Alternatively, or additionally, the analysis of PLIF levels may be effected on the polynucleotide level.

U.S. Pat. No. 7,217,686, incorporated herein by reference discloses polynucleotide primers for detection of PLIF.

According to a particular embodiment, the primers hybridize with the DNA or RNA which encodes an amino acid sequence located in the C terminus of PLIF—for example an amino acid sequence comprised in the last 25 amino acids (SEQ ID NO: 1). According to a particular embodiment, one primers hybridizes with the DNA or RNA which encodes an amino acid sequence comprised in SEQ ID NO: 1, and one primer hybridized with the DNA or RNA which encodes an amino acid sequence further upstream (i.e. towards the N terminus) of the PLIF protein. According to still another embodiment, at least one of the primers hybridizes with the DNA or RNA which encodes the bridging region between SEQ ID NO: 1 and the rest of the PLIF protein.

Methods of analyzing levels of PLIF on the RNA level are described herein below.

Northern Blot Analysis:

This method involves the detection of a particular RNA in a mixture of RNAs. An RNA sample is denatured by treatment with an agent (e.g., formaldehyde) that prevents hydrogen bonding between base pairs, ensuring that all the RNA molecules have an unfolded, linear conformation. The individual RNA molecules are then separated according to size by gel electrophoresis and transferred to a nitrocellulose or a nylon-based membrane to which the denatured RNAs adhere. The membrane is then exposed to labeled DNA probes. Probes may be labeled using radio-isotopes or enzyme linked nucleotides. Detection may be using autoradiography, colorimetric reaction or chemiluminescence. This method allows both quantitation of an amount of particular RNA molecules and determination of its identity by a relative position on the membrane which is indicative of a migration distance in the gel during electrophoresis.

RT-PCR Analysis:

This method uses PCR amplification of relatively rare RNAs molecules. First, RNA molecules are purified from the cells and converted into complementary DNA (cDNA) using a reverse transcriptase enzyme (such as an MMLV-RT) and primers such as, oligo dT, random hexamers or gene specific primers. Then by applying gene specific primers and Taq DNA polymerase, a PCR amplification reaction is carried out in a PCR machine. Those of skills in the art are capable of selecting the length and sequence of the gene specific primers and the PCR conditions (i.e., annealing temperatures, number of cycles and the like) which are suitable for detecting specific RNA molecules. It will be appreciated that a semi-quantitative RT-PCR reaction can be employed by adjusting the number of PCR cycles and comparing the amplification product to known controls.

RNA In Situ Hybridization Stain:

In this method DNA or RNA probes are attached to the RNA molecules present in the cells. Generally, the cells are first fixed to microscopic slides to preserve the cellular structure and to prevent the RNA molecules from being degraded and then are subjected to hybridization buffer containing the labeled probe. The hybridization buffer includes reagents such as formamide and salts (e.g., sodium chloride and sodium citrate) which enable specific hybridization of the DNA or RNA probes with their target mRNA molecules in situ while avoiding non-specific binding of probe. Those of skills in the art are capable of adjusting the hybridization conditions (i.e., temperature, concentration of salts and formamide and the like) to specific probes and types of cells. Following hybridization, any unbound probe is washed off and the bound probe is detected using known methods. For example, if a radio-labeled probe is used, then the slide is subjected to a photographic emulsion which reveals signals generated using radio-labeled probes; if the probe was labeled with an enzyme then the enzyme-specific substrate is added for the formation of a colorimetric reaction; if the probe is labeled using a fluorescent label, then the bound probe is revealed using a fluorescent microscope; if the probe is labeled using a tag (e.g., digoxigenin, biotin, and the like) then the bound probe can be detected following interaction with a tag-specific antibody which can be detected using known methods.

In Situ RT-PCR Stain:

This method is described in Nuovo G J, et al. [Intracellular localization of polymerase chain reaction (PCR)-amplified hepatitis C cDNA. Am J Surg Pathol. 1993, 17: 683-90] and Komminoth P, et al. [Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract. 1994, 190: 1017-25]. Briefly, the RT-PCR reaction is performed on fixed cells by incorporating labeled nucleotides to the PCR reaction. The reaction is carried on using a specific in situ RT-PCR apparatus such as the laser-capture microdissection PixCell I LCM system available from Arcturus Engineering (Mountainview, Calif.).

It will be appreciated that the level of PLIF may be determined following treatment to ascertain treatment efficacy. Thus the prognosis of the cancer following treatment may be followed.

As mentioned, the present invention also contemplates antibodies that are capable of specifically recognizing and binding the multimeric peptides disclosed herein. Preferably, the antibody specifically binds at least one epitope of the peptides described herein that are not present in the full length PLIF polypeptide of C48 peptide. As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')$_2$, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Humanized forms of non-human (e.g., murine) antibodies are also contemplated. Methods of humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321: 522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

As used herein the term "about" refers to ±10%.

The terms "comprises", "comprising", "includes", "including", "having" and their conjugates mean "including but not limited to".

The term "consisting of": means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods

C24D Polypeptide Synthesis:

Synthesis was performed by the fully automated Applied Biosystems Peptide Synthesizer Model 433A.

Fmoc chemistry in general and Fast Moc chemistry was performed.

Starting with Fmoc-Pro-Wang Resin. Side chain protecting group were: Cys(Trt); His((Trt); Arg(Pbf); Lys(Boc); Ser and Thr(tBu).

The remaining amino acids have no protecting group.

After assembly, the protected peptide chain bound to Wang Resin was removed and the peptide-resin anchoring bond was cleaved under acidic conditions.

The crude peptide was purified by HPLC.

Dimerization was performed with the potassium ferricyanide solution, and again purified by HPLC.

C24-48M polypeptide is a monomeric synthetic polypeptide comprising the C48 terminal amino acids (aa) 24-48.

Anti-C24D Immunoglobulin (Ig): Preparation and Specificity:

Mice were immunized with synthetic C24D polypeptide. Each mouse was immunized with 50 µg in 0.050 ml phosphate buffer solution (PBS) mixed with complete Freund's adjuvant (v/v). Injections were carried out on days 1, 7 and 21.

On day 28, the mice were bled and immunoglobulins were isolated by salt precipitation (1).

Figure 1:
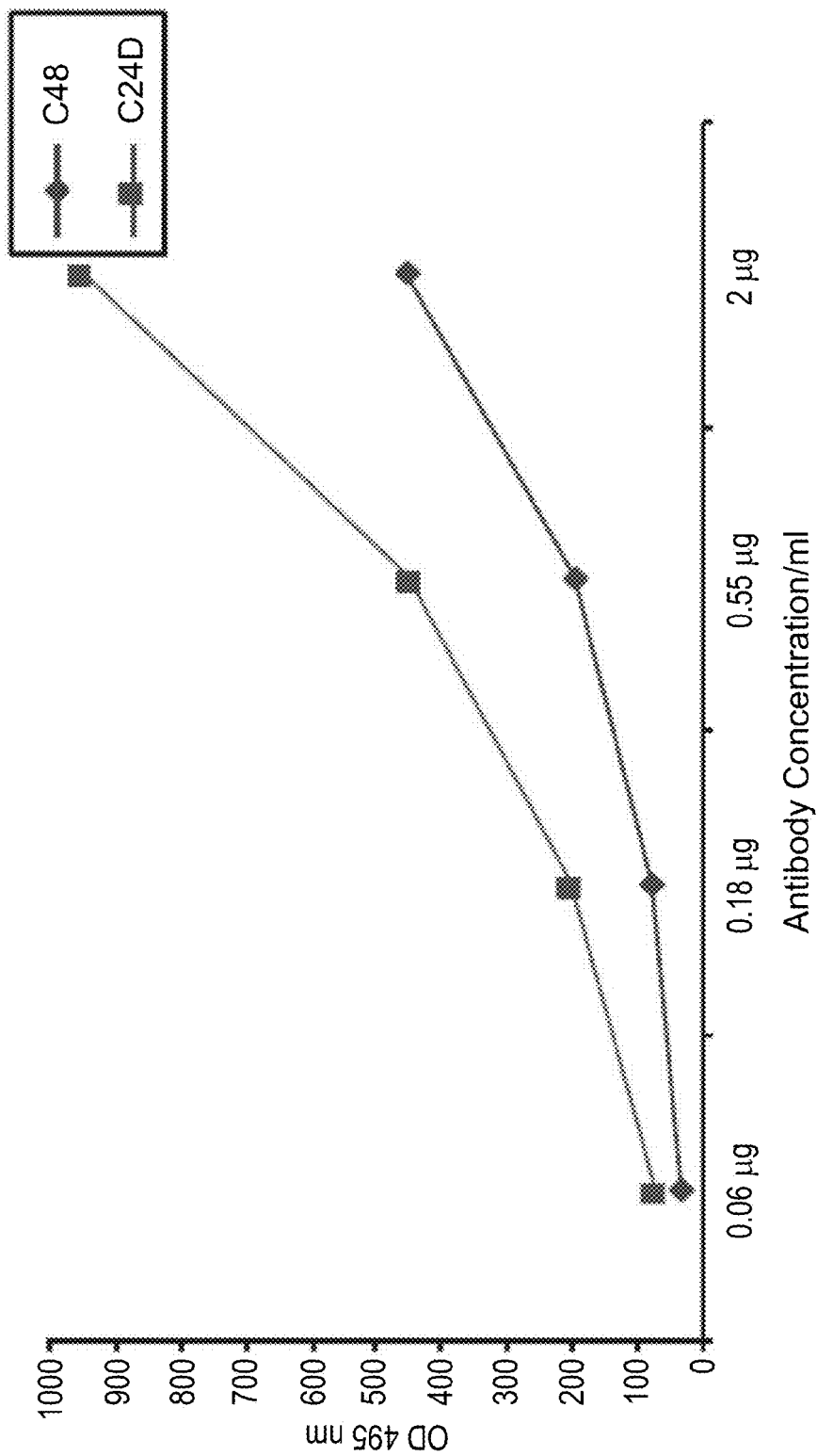

Anti-C24D Specificity:

As shown in FIG. 1, anti-C24D binds to both C24D and C48, in a dose response manner.

Anti-C48 Preparation and Specificity:

Preparation: Anti-C48 was prepared as previously described (1).

Figure 2:
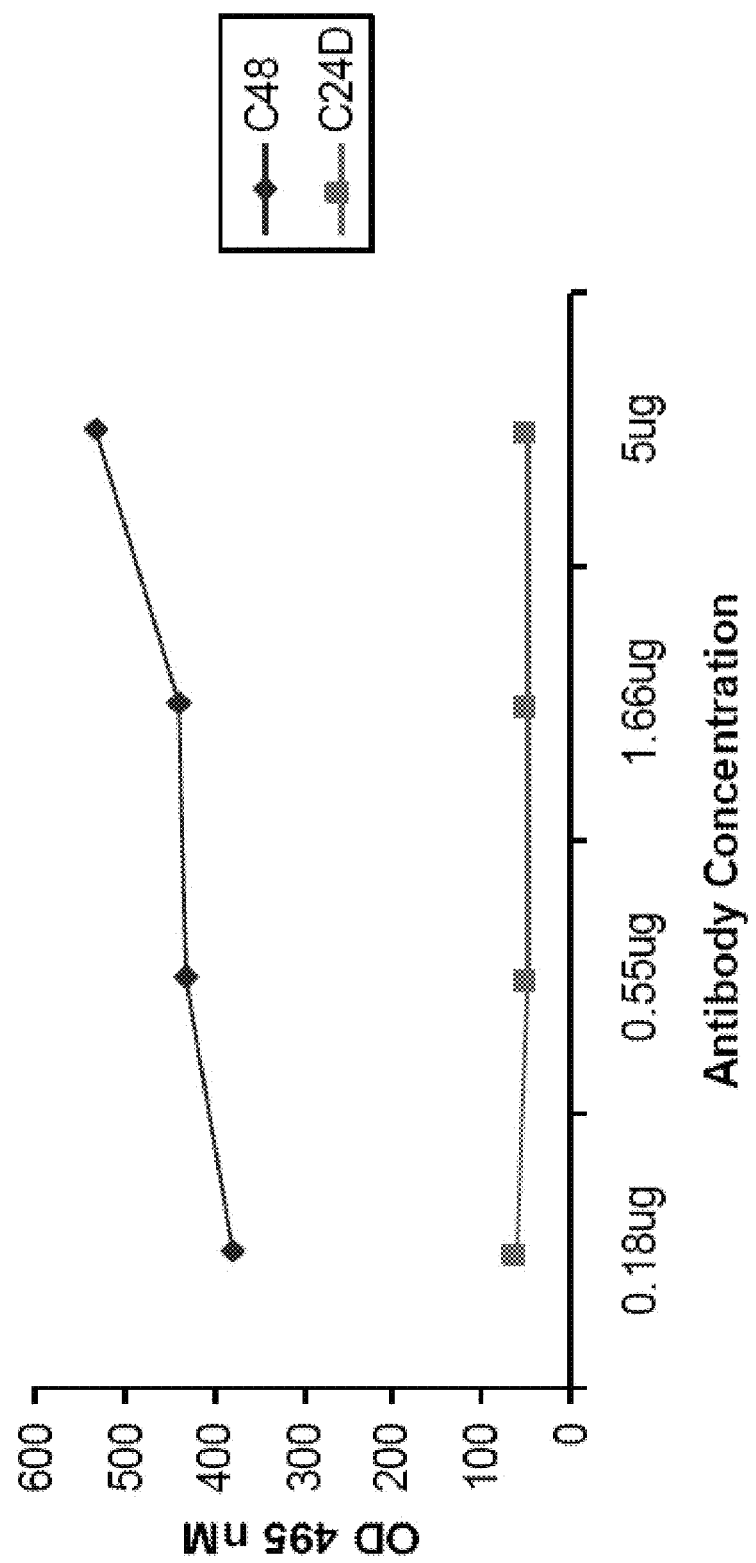

Specificity: Anti-C48 binds exclusively to C48 but does not bind to C24D (FIG. 2).

Antibody Titration by Enzyme-Linked Immunosorbent Assay (ELISA):

ELISA determined the presence of anti-C48 and anti-C24D antibodies as follows: Dynatek microtiter plates (129B) were coated with 100 µl/well of pure C48 or C24D (1 µg/ml) overnight at 4° C. Plates were then washed with PBS containing 0.01% Tween (PBS-T) and blocked for 30 minutes with 1% bovine serum albumin (BSA). Increasing concentrations of antibodies were added to the coated plates and incubated for 1 hour at room temperature. The wells were washed with PBS-T and the bound antibodies were detected with horse-radish peroxidase (HRP)-labeled anti-Rabbit or anti-Mouse IgG, respectively (Dako).

Cell Stimulation and Cytokine Production:

Peripheral blood mononuclear cells (PBMC) at $2 \times 10^6$ in 1 ml of 5% human serum/RPMI-1640 were cultured in a 10 ml round-bottom tube, treated with C48 (2 µg/ml), C24D (10 µg/ml), or non-treated. Subsequently, these cultures were stimulated with OKT3 MoAb (100 ng/ml) or non-stimulated. Supernatants were collected at 24, and 72 hours for analysis of IL-10 and other cytokines as indicated in each experiment.

Cytokine Production Evaluation:

The ELISA kits for the human cytokines TNF-α, IL-10 and IFN-γ were purchased from DPC, and R&D Systems, USA. These kits were used to quantify the indicated cytokines production in the supernatants, according to the manufacturer's instructions.

Breast Cancer Cell Cultures:

The MCF-7 human breast carcinoma cell line was maintained in monolayer cultures in RPMI-1640 medium supplemented with 10% fetal calf serum. For passages, confluent monolayer cultures were trypsinized with trypsin/EDTA solution (0.25%/0.05%, respectively), washed once, and seeded in culture medium.

Human ductal breast epithelial tumor cell line (T47D) was maintained in RPMI-1640 medium supplemented with 10% fetal calf serum.

Preparation of PBMC:

Buffy coats from blood bank donors were layered onto Lymphoprep solution (Nycomed, Oslo, Norway) and spun at 2000 rpm for 20 minutes. The interface layer was collected, washed twice, counted, and resuspended in PBS; pH 7.4 to the desired cell concentration.

MCF-7 and PBMC Co-Culture In Vitro:

MCF-7 was maintained in RPMI+fetal calf serum (FCS) 10%. 1 day before the experimental start, the medium was replaced with RPMI+human AB serum 10%. PBMC ($1 \times 10^6$) were added to MCF-7 ($0.1 \times 10^6$) at a final volume of 1 ml dispensed into 24-well plates. The cells were treated with C24D 30 µg/ml at 0, 24 and 48 hours. The cells without treatment were used as a control. Plates were washed, fixed for 1 hour with 4% formaldehyde solution and stained with Giemsa for microscopic evaluation on experimental days 1, 5, and 8.

T47D and PBMC Co-Culture In Vitro:

T47D was maintained in RPMI+FCS 10%. 1 day before the start of the experiment, the medium was replaced with RPMI+AB human serum 10%. PBMCs ($1 \times 10^6$) were added to T47D ($0.1 \times 10^6$) at a final volume 1 ml into 24-well plates. The cells were treated with C24D (30 µg/ml) at 0, 24 and 48 hours. The cells without treatment were used as a control. Plates were washed, fixed for 1 hour with 4% formaldehyde solution and stained with Giemsa for microscopic evaluation on experimental days 1, 5, and 8.

In Vivo Studies:

Athymic BALB/c nude mice were purchased from Harlan Laboratories Ltd. Mice were inoculated subcutaneously (s.c.) with MCF-7 human breast cancer cells ($6 \times 10^6$), in the presence of an estrogen source (0.72 mg). The slow-release pellets (60-day release) were implanted s.c. into the cervical scapular space.

Preparation and Transfusion of Human PBMC:

Buffy coats from blood bank donors were layered onto Lymphoprep solution (Nycomed, Oslo, Norway) and spun at 2000 rpm for 20 minutes. The interface layer was collected, washed twice, counted, and resuspended in PBS (pH 7.4) to the desired cell concentration. Human PBMC ($50 \times 10^6/0.5$ ml) were injected intravenously after transplantation of MCF-7 tumor cells as described above.

Treatment of Tumor-Bearing Mice with C24D:

In each experiment, mice were divided into groups of five. C24D dissolved in PBS pH 7.2 was injected i.p. to each mouse daily, at an optimal dose of 60 µg/0.2 ml. Control mice received daily injections of PBS.

Gross and Microscopic Pathology:

Tumors were excised, measured, and fixed in phosphate-buffer formalin (pH 7.0) from which paraffin embedded blocks were prepared.

Immunohistochemistry:

Four-micron tissue sections were cut from paraffin-embedded blocks and mounted on coated super frost plus slides. They were deparaffinized in xylene, and rehydrated with graded alcohols, rinsed in $H_2O$, and then incubated in 3% $H_2O_2$ for 10 minutes and washed in $H_2O$.

For antigen unmasking, the sections were heated in 10 mM of sodium citrate buffer (pH 6.0) for 10 minutes in microwaves or pressure chambers, depending on the manufacturer's instructions, and then cooled at room temperature for 20 minutes. Slides were washed in $H_2O$ and in PBS buffer for 5 minutes.

Slides were incubated in normal serum for 10 minutes from a kit (Zymed Laboratories, San Francisco, Calif.). For immunohistochemical staining, performed manually, slides were incubated with primary antibodies at previously determined optimal concentrations, for 60 minutes at room temperature, as summarized in Table 4, herein below.

TABLE 4

| Antibody | Cellular Distribution | Origin | Positive Control |
|---|---|---|---|
| LCA | All leukocytes | Biogenex | Tonsil |

Slides were washed in $H_2O$ and in PBS buffer for 5 minutes and further incubated for 10 minutes with a biothylated second antibody (Zymed Laboratories, San Francisco, Calif.), followed by PBS. Slides were then incubated for 10 minutes with conjugated streptavidin peroxidase (Zymed Laboratories), washed with PBS, incubated with 3,3'-Diaminobenzidine (Zymed Laboratories, San Francisco, Calif.) for 5 minutes and further washed with PBS. The stained slides were counterstained with Mayer's haematoxylin and mounted with aqueous mounting solution.

Statistical Analysis:

Results were presented as mean±standard deviation. Comparisons were made by Student's t test. P values of less than or equal to 0.05 were considered statistically significant.

Example 1

C24D Construction and Synthesis

Figure 4:
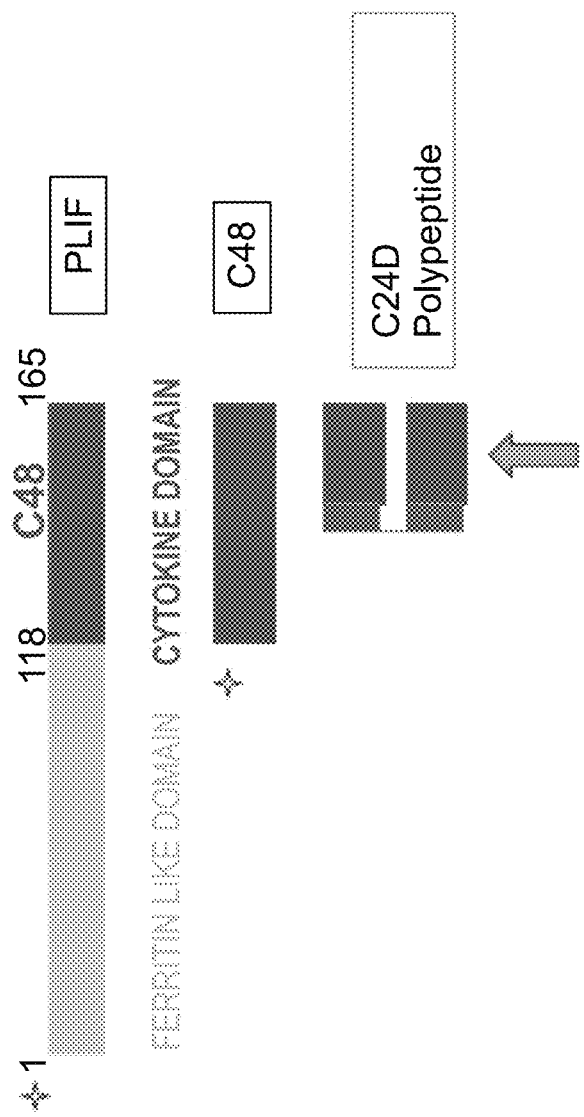
Figure 5:
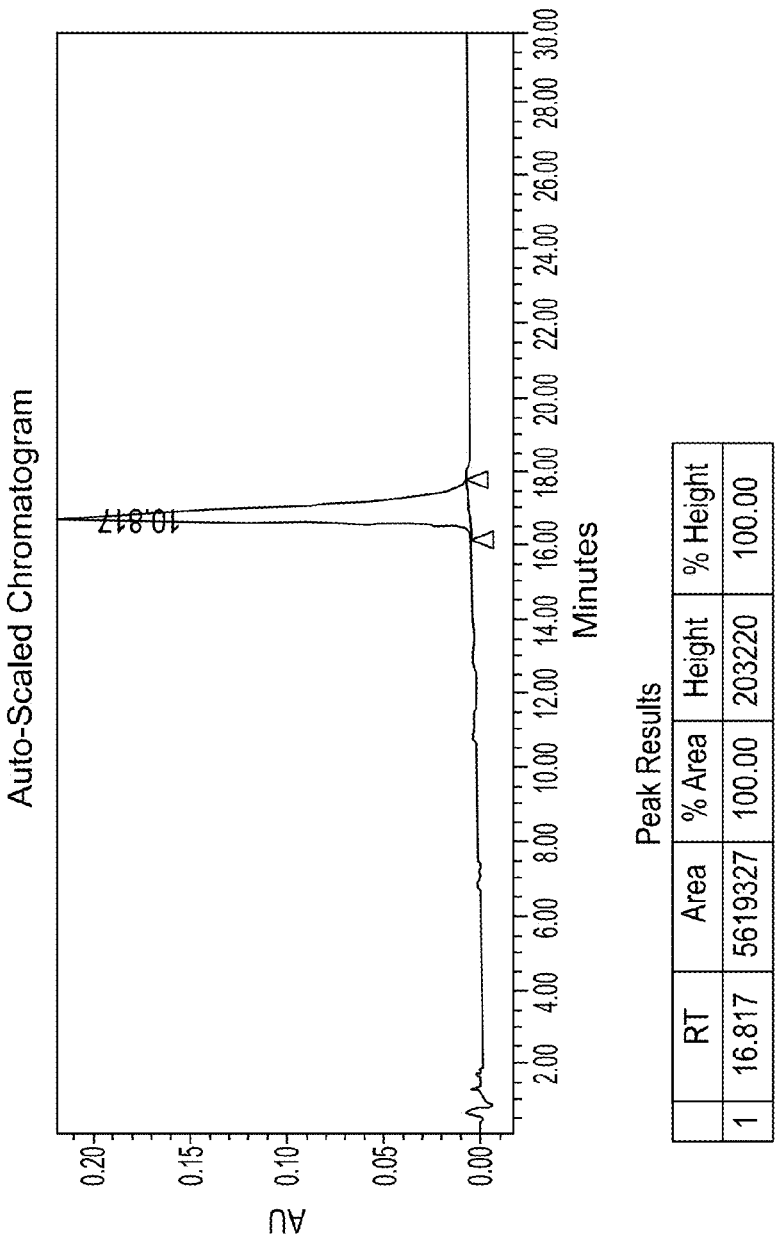

C24D is a covalently linked dimer of identical polypeptide chains, each polypeptide chain being set forth by SEQ ID NO: 1, and further comprising at the N-terminal end the amino acids Cysteine and Glycine. SEQ ID NO: 1 corresponds to the amino acids homologous to the sequence of amino acids 25-48 of recombinant-C48 protein (FIGS. 3-5).

C24D is composed of 54 amino acids and is set forth by SEQ ID NO: 102.

Molecular weight (mw): 6418.8
Average hydrophobicity: 0.2.
Net change at pH 7.0: 7.2, isoelectric point PI:12.7

Example 2

Bioactivity of C24D In Vitro

Binding of C48 to Human Macrophages Detected by Anti-C48 and Anti-C24D Antibodies:

C48 binds to the surface of human macrophages, as detected by both mouse anti-C24D IgG-FITC (FIG. 6A), and rabbit anti-C48 IgG-FITC (FIG. 6B).

Binding of C24D to Human T Cells:

Comparison with C48 and C24-48M: As seen in FIG. 7A, C48 and C24D bind similarly to the surface of human T cells (HDMAR), whereas C24-48M does not (FIG. 7B). Furthermore, pre-incubation of T cells with different concentrations of C24D (FIGS. 8A,B) inhibited the binding of C48 to T cells as detected by the specific anti-C48 IgG-FITC (FIGS. 8A,B). These results suggest that C24D binds competitively to the C48 receptor on human T cells.

Effect of C24D on Secretion of IL-10 and INF-γ by Human PBMC:

The effect of C24D peptide on cytokine secretion of OKT3 activated human PBMC and on C48-treated PBMC was investigated. As seen in FIG. 9, C24D increased significantly the level of INF-γ after 72 hours of culture compared to control cultures and even in the presence of C48. C48 did not affect the INF-γ level. Yet, as seen in FIG. 9, C24D did not increase the level of IL-10 compared to the control cells, but when added to the culture together with C48, C24D decreased the high level of IL-10 normally induced by C48 (FIG. 10).

These results indicate that C24D treatment of activated human lymphocytes results in the switching of the TH2 diminished type immune response induced by C48 into the TH1 type vigorous response.

Effect of C24D Treatment on In Vitro Cultures of MCF-7 Human Breast Cancer Cells and Human PBMC:

MCF-7 tumor cells grow as a monolayer in tissue culture plates (FIG. 11A). The addition of PBMC to tumor cells at a ratio of 10:1 did not affect their growth (FIG. 11B). Treatment with C24D of MCF-7 and PBMC cultured for 8 days at 37° C. resulted in lysis of the cancer cells, leaving adherent PBMC on the tissue culture plate (FIG. 11C), similar to the control PBMC-only culture (FIG. 11D).

FIG. 12 illustrates Giemsa staining of the C24D-treated MCF-7 cell monolayer lysis (A) compared with and MCF-7 cell monolayer of the control culture (B).

Further experiments were performed to test the cytotoxic effects of the MCF-7-activated and C24D-treated PBMC on a secondary MCF-7 cell culture. PBMC were removed from the following cell cultures: a) non-treated control MCF-7+PBMC, b) control (only PBMC cultured with C24D), and c) C24D-treated MCF-7+PBMC. All were transferred to new untreated MCF-7 cell monolayer cultures. The results demonstrated that whereas PBMC from control cultures (FIGS. 13A,B) were not cytotoxic to MCF-7 cells, PBMC removed from C24D-treated MCF-7 cultures were cytotoxic to the tumor cells (FIG. 13C). These results indicate the activation and proliferation of anti-tumor specific cytotoxic cells.

Example 3

Therapeutic Effect of C24D on MCF-7 Tumor Development in Nude Mice

Nude mice were implanted s.c. with MCF-7 tumor cells, transfused with human PBMC, and treated by daily i.p. injections of C24D. Control mice received PBS injections for comparison.

After 19 days, the mice were sacrificed and the tumors removed and measured. As seen in FIGS. 14 and 15, treatment with C24D inhibited significantly the tumor growth, mean tumor volume 42.5±14 mm$^3$ for C24D-treated tumors vs. 188.5±34 mm$^3$ for untreated controls (p=0.015).

Immunohistochemical Characterization:

Histochemical analyses of the tumors derived from immune-compromised mice treated with C24D and controls were performed. Large areas of tumoral necrosis were seen in tumors removed from the C24D-treated mice, compared to minimal or no necrosis from the control mice (FIG. 16). Immunohistochemical staining with anti-CD45 MoAb was performed. FIG. 16 shows images obtained from representative tumors. As seen, a specimen obtained from the C24D-treated group, exhibited massive necrotic areas with intratumor infiltration of human CD45+ cells (brown staining). This is in sharp contrast to the absence of CD45+ cells in the PBS-treated specimen (FIG. 16) (×40).

Example 4

Effect of C24D on T47D Cells

T47D tumor cells grow as a monolayer in tissue culture plates (FIG. 17A). The addition of PBMC to tumor cells at a ratio of 10:1 did not affect their growth (FIG. 17B). Treatment of T47D cells with C24D and PBMC cultured for 5 days at 37° C. resulted in lysis of the cancer cells, leaving adherent PBMC on the tissue culture plate (FIG. 17C). An increase in tumor cell lysis can be seen after 7 days of incubation with C24D and PBMCs (FIGS. 18A-C).

Further experiments were performed to test the cytotoxic effects of the T47D-activated and C24D-treated PBMC on a secondary T47D cell culture. After five days of primary culture with T47D and C24D, PBMCs (1 million) were added to fresh T47D (0.1 million) at a final volume 1 ml into 24-well plates. The cells were treated with C24D (30 μg/ml) at 0, 24 and 48 hours. After 4 days of culture, the cells were examined. FIGS. 19A-C illustrate the cytotoxic effect of C24D on the T47D cells when incubated together with PBMCs In another experiment, PBMCs were incubated for 7 days with T47D cells and C24D, centrifuged and transferred to 96 well plates which had been seeded 24 hours previously with T47D cells.

The ratio between T47D and PBMCs was 1:10. Two days after incubation the cells were examined as illustrated in FIGS. 20A-B.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Moroz Ch, Traub L, Maymon R, Zahalka M. PLIF—a novel human ferritin subunit from placenta with immunosuppressive activity. J Biol Chem 2002; 277:2901-12905.
2. Moroz Ch. U.S. Pat. No. 7,217,686B1.
3. Maymon R, Jauniaux E, Greenwold N, Moroz Ch. Localization of p43 placental isoferritin in human feto-maternal tissue interface. Am J Obstet Gynecol 2000; 182; 670-674.
4. Zahalka M A, Barak V, Traub L, Moroz C. PLIF induces IL-10 production in monocytes; a calmodulin-p38 mitogen-activated protein kinase dependent pathway. FASEB J 2003; 17:955-957.
5. Moroz C, Grunspan A, Zahalka M A, Traub L, Kodman Y, Yaniv I. Treatment of human bone marrow with recombinant placenta immunoregulator ferritin (PLIF) results in myelopoiesis and T cell suppression through modulation of the cytokine-chemokine networks. Exp Hematol 2006; 34:159-166.
6. Sirota L, Kupfer B, Moroz Ch. Placental isoferritin as a physiological downregulator of cellular immunoreactivity during pregnancy. Clin Exp Immunol 1989; 77:257-262.
7. Moroz Ch, Livni E, Segal J. Treatment of recurrent spontaneous abortions by immunization with paternal lymphocytes induce immunosuppression by placental isoferritin (PLF). Am J Reprod Immun 1993; 30:32-6.
8. Maymon R, Moroz Ch. Placental isoferritin: a new biomarker from conception to delivery. Br J Obstet Gynecol 1996; 103:301-305.
9. Fisch B, Manor Y, Ovadia J, Moroz Ch. Placental isoferritin as a marker of early abortions in pregnancies induced by in vitro fertilization. Placenta 1996; 17:247-251.
10. Maymon R, Bahari C, Moroz Ch. Placental isoferritin measured by a specific monoclonal antibody as a new predictive marker for premature contraction outcome. Obstet Gynecol 1989; 74:1-3.
11. Rosen A C, Rosen H R, Huber, K., Ausch, Ch., Klein, M., Moroz Ch. Correlation of placental isoferritin with birthweight and time point of first contractions. Obstet. Gynecol Invest 1995; 39:11-14.
12. Bar J, Maymon R, Hod M, Manor Y, Moroz Ch. Low serum placental isoferritin in pregnant women at risk of developing preeclampsia. Hyperten Pregn 1998; 17:315-321.
13. Nahum R, Brenner O, Zahalka M A, Traub L, Quintana F, Moroz C. Blocking of the placental immune-modulator PLIF activated Th1 type cytokines and affected placenta development, fetal growth and the pregnancy outcome. Hum Reprod 2004; 19(3): 715-722.
14. Moroz C, Traub L, Rabizadeh E, Zahalka M A. A proof of concept study: Human C48-placenta immunoregulatory factor is an effective, single therapeutic agent enabling allogeneic, nonmanipulated murine bone marrow transplantation. Exp Hematol 2009; 37: 1121-1130.
14. Halpern M, Zahalka M A, Traub L, Moroz C. Antibodies to placental Immunoregulatory ferritin (PLIF) with transfer of polyclonal lymphocytes arrests MCF-7 human breast cancer growth in nude mouse model. Neoplasia 2007; 9: 447-494.
15. Moroz Ch, Bessler H, Lurie Y, Shaklai M. A new monoclonal antibody enzymoassay for the specific measurement of placental ferritin isotype in hematologic malignancies. Exp Hematol 1987; 15:258-262.
16. Rosen H R, Moroz Ch, Reiner A, Stierer M, Svec J, Reinerova M, Schemper M, Jakesz R. Expression of p43 in breast cancer tissue, correlation with prognostic parameters. Cancer Lett 1992; 67:35-45.
17. Moroz Ch, Kahn M, Ron E, Luria H, Chaimoff C. The use of oncofetal ferritin bearing lymphocytes as a marker for screening, diagnosis and follow-up of patients with early breast malignancy: screening of 3400 women. Cancer 1989; 64:123-129.
18. Rosen H R, Ausch C, Reiner G, Reinerova M, Svec J, Tuchler H, Schiessel R, Moroz Ch. Downregulation of lymphocyte mitogenesis by breast cancer-associated p43. Cancer Lett 1994; 82:105-111.

What is claimed is:

1. A dimer comprising two identical peptide monomers covalently linked to one another, each of said two peptide monomers comprising the amino acid sequence as set forth in SEQ ID NO: 1, wherein said two peptide monomers are no longer than 30 amino acids, wherein the dimer is capable of reducing binding of Placenta Immunomodulatory Factor (PLIF) to human leukocytes.

2. The dimer of claim 1, wherein the peptide is capable of increasing INF-γ secretion from activated leukocytes.

3. The dimer of claim 1, wherein each of said two peptide monomers is attached to a Cysteine (Cys) residue.

4. The dimer of claim 3, wherein the caboxy end of said two peptide monomers is attached to said Cys residue.

5. The dimer of claim 4, wherein each of said two peptide monomers comprise the amino acid sequence as set forth in SEQ ID NO: 101.

6. The dimer of claim 1, wherein each of said two peptide monomers are attached via a non-peptide linker.

7. The dimer of claim 3, wherein said two peptide monomers are linked to one another by a disulfide bond.

8. The dimer of claim 7, wherein said disulfide bond is an intermolecular disulfide bond formed between said Cys residues.

9. The dimer of claim 3, further comprises a Gly residue connecting said Cys residue to said carboxy end of said two peptide monomers.

10. The dimer of claim 1 comprising at least one synthetic amino acid.

11. A pharmaceutical composition comprising the dimer of claim 1 as an active agent and a pharmaceutically acceptable carrier.

12. A dimer comprising two identical peptide monomers covalently linked to one another, each of said two peptide monomers comprising the amino acid sequence as set forth in SEQ ID NO: 1, wherein said two peptide monomers are no longer than 30 amino acids, wherein the dimer is capable of increasing INF-γ secretion from activated leukocytes.

13. The dimer of claim 12, wherein each of said two peptide monomers is attached to a Cysteine (Cys) residue.

14. The dimer of claim 13, wherein the caboxy end of said two peptide monomers is attached to said Cys residue.

15. The dimer of claim 14, wherein each of said two peptide monomers comprise the amino acid sequence as set forth in SEQ ID NO: 101.

16. The dimer of claim 12, wherein each of said two peptide monomers are attached via a non-peptide linker.

17. The dimer of claim 13, wherein said two peptide monomers are linked to one another by a disulfide bond.

18. The dimer of claim 17, wherein said disulfide bond is an intermolecular disulfide bond formed between said Cys residues.

19. The dimer of claim 13, further comprises a Gly residue connecting said Cys residue to said carboxy end of said two peptide monomers.

20. The dimer of claim 12 comprising at least one synthetic amino acid.

21. A pharmaceutical composition comprising the dimer of claim 12 as an active agent and a pharmaceutically acceptable carrier.

22. A dimer comprising two identical peptide monomers covalently linked to one another, wherein each of said two peptide monomers consist of the amino acid sequence as set forth in SEQ ID NO: 101.

23. A pharmaceutical composition comprising the dimer of claim 22 as an active agent and a pharmaceutically acceptable carrier.

24. A dimer comprising two identical peptide monomers linked to one another by a disulfide bond, wherein each of said two peptide monomers comprise the amino acid sequence as set forth in SEQ ID NO: 101, wherein the dimer is capable of reducing binding of Placenta Immunomodulatory Factor (PLIF) to human leukocytes.

25. A dimer comprising two identical peptide monomers linked to one another by a disulfide bond, wherein each of said two peptide monomers comprise the amino acid sequence as set forth in SEQ ID NO: 101, wherein the dimer is capable of increasing INF-γ secretion from activated leukocytes.

* * * * *

SEQUENCE LISTING

```
<160> NUMBER OF SEQ ID NOS: 102

<210> SEQ ID NO 1
<211> LENGTH: 25
<212> TYPE: PRT
<213> ORGANISM: Artificial sequence
<220> FEATURE:
<223> OTHER INFORMATION: Placental Immunoregulatory Ferritin (PLIF)
      derived polypeptide sequence

<400> SEQUENCE: 1

His His Leu Leu Arg Pro Arg Arg Arg Lys Arg Pro His Ser Ile Pro
1               5                   10                  15

Thr Pro Ile Leu Ile Phe Arg Ser Pro
```

20                  25

<210> SEQ ID NO 2
<211> LENGTH: 13
<212> TYPE: PRT
<213> ORGANISM: Artificial sequence
<220> FEATURE:
<223> OTHER INFORMATION: A monomer of the multimeric peptide

<400> SEQUENCE: 2

His Ser Ile Pro Thr Pro Ile Leu Ile Phe Arg Ser Pro
1               5                   10

<210> SEQ ID NO 3
<211> LENGTH: 14
<212> TYPE: PRT
<213> ORGANISM: Artificial sequence
<220> FEATURE:
<223> OTHER INFORMATION: A monomer of the multimeric peptide

<400> SEQUENCE: 3

His Leu Leu Arg Pro Arg Arg Arg Lys Arg Pro His Ser Ile
1               5                   10

<210> SEQ ID NO 4
<211> LENGTH: 12
<212> TYPE: PRT
<213> ORGANISM: Artificial sequence
<220> FEATURE:
<223> OTHER INFORMATION: A monomer of the multimeric peptide

<400> SEQUENCE: 4

Arg Pro Arg Arg Arg Lys Arg Pro His Ser Ile Pro
1               5                   10

<210> SEQ ID NO 5
<211> LENGTH: 12
<212> TYPE: PRT
<213> ORGANISM: Artificial sequence
<220> FEATURE:
<223> OTHER INFORMATION: A monomer of the multimeric peptide

<400> SEQUENCE: 5

Ser Ile Pro Thr Pro Ile Leu Ile Phe Arg Ser Pro
1               5                   10

<210> SEQ ID NO 6
<211> LENGTH: 14
<212> TYPE: PRT
<213> ORGANISM: Artificial sequence
<220> FEATURE:
<223> OTHER INFORMATION: A monomer of the multimeric peptide

<400> SEQUENCE: 6

Pro His Ser Ile Pro Thr Pro Ile Leu Ile Phe Arg Ser Pro
1               5                   10

<210> SEQ ID NO 7
<211> LENGTH: 11
<212> TYPE: PRT
<213> ORGANISM: Artificial sequence
<220> FEATURE:
<223> OTHER INFORMATION: A monomer of the multimeric peptide

<400> SEQUENCE: 7

His His Leu Leu Arg Pro Arg Arg Arg Lys Arg
1               5                   10

```
<210> SEQ ID NO 8
<211> LENGTH: 15
<212> TYPE: PRT
<213> ORGANISM: Artificial sequence
<220> FEATURE:
<223> OTHER INFORMATION: Exemplary monomer of the multimeric peptide

<400> SEQUENCE: 8

Cys Gly His Ser Ile Pro Thr Pro Ile Leu Ile Phe Arg Ser Pro
1               5                   10                  15

<210> SEQ ID NO 9
<211> LENGTH: 16
<212> TYPE: PRT
<213> ORGANISM: Artificial sequence
<220> FEATURE:
<223> OTHER INFORMATION: Exemplary monomer of the multimeric peptide

<400> SEQUENCE: 9

Cys Gly His Leu Leu Arg Pro Arg Arg Arg Lys Arg Pro His Ser Ile
1               5                   10                  15

<210> SEQ ID NO 10
<211> LENGTH: 14
<212> TYPE: PRT
<213> ORGANISM: Artificial sequence
<220> FEATURE:
<223> OTHER INFORMATION: Exemplary monomer of the multimeric peptide

<400> SEQUENCE: 10

Cys Gly Arg Pro Arg Arg Arg Lys Arg Pro His Ser Ile Pro
1               5                   10

<210> SEQ ID NO 11
<211> LENGTH: 14
<212> TYPE: PRT
<213> ORGANISM: Artificial sequence
<220> FEATURE:
<223> OTHER INFORMATION: Exemplary monomer of the multimeric peptide

<400> SEQUENCE: 11

Cys Gly Ser Ile Pro Thr Pro Ile Leu Ile Phe Arg Ser Pro
1               5                   10

<210> SEQ ID NO 12
<211> LENGTH: 16
<212> TYPE: PRT
<213> ORGANISM: Artificial sequence
<220> FEATURE:
<223> OTHER INFORMATION: Exemplary monomer of the multimeric peptide

<400> SEQUENCE: 12

Cys Gly Pro His Ser Ile Pro Thr Pro Ile Leu Ile Phe Arg Ser Pro
1               5                   10                  15

<210> SEQ ID NO 13
<211> LENGTH: 13
<212> TYPE: PRT
<213> ORGANISM: Artificial sequence
<220> FEATURE:
<223> OTHER INFORMATION: Exemplary monomer of the multimeric peptide

<400> SEQUENCE: 13

Cys Gly His His Leu Leu Arg Pro Arg Arg Arg Lys Arg
1               5                   10
```

```
<210> SEQ ID NO 14
<211> LENGTH: 15
<212> TYPE: PRT
<213> ORGANISM: Artificial sequence
<220> FEATURE:
<223> OTHER INFORMATION: Placental Immunoregulatory Ferritin (PLIF)
      derived polypeptide sequence

<400> SEQUENCE: 14

Arg Pro His Ser Ile Pro Thr Pro Ile Leu Ile Phe Arg Ser Pro
1               5                   10                  15

<210> SEQ ID NO 15
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 15

His His Leu Leu Arg Pro
1               5

<210> SEQ ID NO 16
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 16

His Leu Leu Arg Pro Arg
1               5

<210> SEQ ID NO 17
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 17

Leu Leu Arg Pro Arg Arg
1               5

<210> SEQ ID NO 18
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 18

Leu Arg Pro Arg Arg Lys
1               5

<210> SEQ ID NO 19
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 19

Arg Pro Arg Arg Lys Arg
1               5
```

```
<210> SEQ ID NO 20
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 20

Pro Arg Arg Lys Arg Pro
1               5

<210> SEQ ID NO 21
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 21

Arg Arg Lys Arg Pro His
1               5

<210> SEQ ID NO 22
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 22

Arg Lys Arg Pro His Ser
1               5

<210> SEQ ID NO 23
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 23

Lys Arg Pro His Ser Ile
1               5

<210> SEQ ID NO 24
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 24

Arg Pro His Ser Ile Pro
1               5

<210> SEQ ID NO 25
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 25

Pro His Ser Ile Pro Thr
1               5
```

```
<210> SEQ ID NO 26
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 26

His Ser Ile Pro Thr Pro
1               5

<210> SEQ ID NO 27
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 27

Ser Ile Pro Thr Pro Ile
1               5

<210> SEQ ID NO 28
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 28

Ile Pro Thr Pro Ile Leu
1               5

<210> SEQ ID NO 29
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 29

Pro Thr Pro Ile Leu Ile
1               5

<210> SEQ ID NO 30
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 30

Thr Pro Ile Leu Ile Phe
1               5

<210> SEQ ID NO 31
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 31

Pro Ile Leu Ile Phe Arg
1               5

<210> SEQ ID NO 32
```

```
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 32

Ile Leu Ile Phe Arg Ser
1               5

<210> SEQ ID NO 33
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 33

Leu Ile Phe Arg Ser Pro
1               5

<210> SEQ ID NO 34
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 34

His His Leu Leu Arg Pro Arg
1               5

<210> SEQ ID NO 35
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 35

His Leu Leu Arg Pro Arg Arg
1               5

<210> SEQ ID NO 36
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 36

Leu Leu Arg Pro Arg Arg Lys
1               5

<210> SEQ ID NO 37
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 37

Leu Arg Pro Arg Arg Lys Arg
1               5

<210> SEQ ID NO 38
<211> LENGTH: 7
```

```
<212> TYPE: PRT
<213> ORGANISM: Artificial sequence
<220> FEATURE:
<223> OTHER INFORMATION: Exemplary monomer of the multimeric peptide

<400> SEQUENCE: 38

Arg Pro Arg Arg Lys Arg Pro
1               5

<210> SEQ ID NO 39
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 39

Pro Arg Arg Lys Arg Pro His
1               5

<210> SEQ ID NO 40
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 40

Arg Arg Lys Arg Pro His Ser
1               5

<210> SEQ ID NO 41
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 41

Arg Lys Arg Pro His Ser Ile
1               5

<210> SEQ ID NO 42
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 42

Lys Arg Pro His Ser Ile Pro
1               5

<210> SEQ ID NO 43
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 43

Arg Pro His Ser Ile Pro Thr
1               5

<210> SEQ ID NO 44
<211> LENGTH: 7
<212> TYPE: PRT
```

<213> ORGANISM: Artificial sequence
<220> FEATURE:
<223> OTHER INFORMATION: Exemplary monomer of the multimeric peptide

<400> SEQUENCE: 44

Pro His Ser Ile Pro Thr Pro
1               5

<210> SEQ ID NO 45
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 45

His Ser Ile Pro Thr Pro Ile
1               5

<210> SEQ ID NO 46
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 46

Ser Ile Pro Thr Pro Ile Leu
1               5

<210> SEQ ID NO 47
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 47

Ile Pro Thr Pro Ile Leu Ile
1               5

<210> SEQ ID NO 48
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 48

Pro Thr Pro Ile Leu Ile Phe
1               5

<210> SEQ ID NO 49
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 49

Thr Pro Ile Leu Ile Phe Arg
1               5

<210> SEQ ID NO 50
<211> LENGTH: 7
<212> TYPE: PRT
<213> ORGANISM: Artificial sequence

```
<220> FEATURE:
<223> OTHER INFORMATION: Exemplary monomer of the multimeric peptide

<400> SEQUENCE: 50

Pro Ile Leu Ile Phe Arg Ser
1               5

<210> SEQ ID NO 51
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 51

Ile Leu Ile Phe Arg Ser Pro
1               5

<210> SEQ ID NO 52
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 52

His His Leu Leu Arg Pro Arg Arg
1               5

<210> SEQ ID NO 53
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 53

His Leu Leu Arg Pro Arg Arg Lys
1               5

<210> SEQ ID NO 54
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 54

Leu Leu Arg Pro Arg Arg Lys Arg
1               5

<210> SEQ ID NO 55
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 55

Leu Arg Pro Arg Arg Lys Arg Pro
1               5

<210> SEQ ID NO 56
<211> LENGTH: 8
<212> TYPE: PRT
<213> ORGANISM: Artificial sequence
<220> FEATURE:
```

<223> OTHER INFORMATION: Exemplary monomer of the multimeric peptide

<400> SEQUENCE: 56

Arg Pro Arg Arg Lys Arg Pro His
1               5

<210> SEQ ID NO 57
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 57

Pro Arg Arg Lys Arg Pro His Ser
1               5

<210> SEQ ID NO 58
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 58

Arg Arg Lys Arg Pro His Ser Ile
1               5

<210> SEQ ID NO 59
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 59

Arg Lys Arg Pro His Ser Ile Pro
1               5

<210> SEQ ID NO 60
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 60

Lys Arg Pro His Ser Ile Pro Thr
1               5

<210> SEQ ID NO 61
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 61

Arg Pro His Ser Ile Pro Thr Pro
1               5

<210> SEQ ID NO 62
<211> LENGTH: 8
<212> TYPE: PRT
<213> ORGANISM: Artificial sequence
<220> FEATURE:
<223> OTHER INFORMATION: Exemplary monomer of the multimeric peptide

```
<400> SEQUENCE: 62

Pro His Ser Ile Pro Thr Pro Ile
1               5

<210> SEQ ID NO 63
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 63

His Ser Ile Pro Thr Pro Ile Leu
1               5

<210> SEQ ID NO 64
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 64

Ser Ile Pro Thr Pro Ile Leu Ile
1               5

<210> SEQ ID NO 65
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 65

Ile Pro Thr Pro Ile Leu Ile Phe
1               5

<210> SEQ ID NO 66
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 66

Pro Thr Pro Ile Leu Ile Phe Arg
1               5

<210> SEQ ID NO 67
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 67

Thr Pro Ile Leu Ile Phe Arg Ser
1               5

<210> SEQ ID NO 68
<211> LENGTH: 8
<212> TYPE: PRT
<213> ORGANISM: Artificial sequence
<220> FEATURE:
<223> OTHER INFORMATION: Exemplary monomer of the multimeric peptide
```

```
<400> SEQUENCE: 68

Pro Ile Leu Ile Phe Arg Ser Pro
1               5

<210> SEQ ID NO 69
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 69

His His Leu Leu Arg Pro Arg Arg Lys
1               5

<210> SEQ ID NO 70
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 70

His Leu Leu Arg Pro Arg Arg Lys Arg
1               5

<210> SEQ ID NO 71
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 71

Leu Leu Arg Pro Arg Arg Lys Arg Pro
1               5

<210> SEQ ID NO 72
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 72

Leu Arg Pro Arg Arg Lys Arg Pro His
1               5

<210> SEQ ID NO 73
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 73

Arg Pro Arg Arg Lys Arg Pro His Ser
1               5

<210> SEQ ID NO 74
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 74
```

Pro Arg Arg Lys Arg Pro His Ser Ile
1               5

<210> SEQ ID NO 75
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 75

Arg Arg Lys Arg Pro His Ser Ile Pro
1               5

<210> SEQ ID NO 76
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 76

Arg Lys Arg Pro His Ser Ile Pro Thr
1               5

<210> SEQ ID NO 77
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 77

Lys Arg Pro His Ser Ile Pro Thr Pro
1               5

<210> SEQ ID NO 78
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 78

Arg Pro His Ser Ile Pro Thr Pro Ile
1               5

<210> SEQ ID NO 79
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 79

Pro His Ser Ile Pro Thr Pro Ile Leu
1               5

<210> SEQ ID NO 80
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 80

His Ser Ile Pro Thr Pro Ile Leu Ile
1               5

<210> SEQ ID NO 81
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 81

Ser Ile Pro Thr Pro Ile Leu Ile Phe
1               5

<210> SEQ ID NO 82
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 82

Ile Pro Thr Pro Ile Leu Ile Phe Arg
1               5

<210> SEQ ID NO 83
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 83

Pro Thr Pro Ile Leu Ile Phe Arg Ser
1               5

<210> SEQ ID NO 84
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 84

Thr Pro Ile Leu Ile Phe Arg Ser Pro
1               5

<210> SEQ ID NO 85
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 85

His His Leu Leu Arg Pro Arg Arg Lys Arg
1               5                   10

<210> SEQ ID NO 86
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 86

His Leu Leu Arg Pro Arg Arg Lys Arg Pro

<210> SEQ ID NO 87
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 87

Leu Leu Arg Pro Arg Arg Lys Arg Pro His
1               5                   10

<210> SEQ ID NO 88
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 88

Leu Arg Pro Arg Arg Lys Arg Pro His Ser
1               5                   10

<210> SEQ ID NO 89
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 89

Arg Pro Arg Arg Lys Arg Pro His Ser Ile
1               5                   10

<210> SEQ ID NO 90
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 90

Pro Arg Arg Lys Arg Pro His Ser Ile Pro
1               5                   10

<210> SEQ ID NO 91
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 91

Arg Arg Lys Arg Pro His Ser Ile Pro Thr
1               5                   10

<210> SEQ ID NO 92
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 92

Arg Lys Arg Pro His Ser Ile Pro Thr Pro
1               5                   10

<210> SEQ ID NO 93
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 93

Lys Arg Pro His Ser Ile Pro Thr Pro Ile
1               5                   10

<210> SEQ ID NO 94
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 94

Arg Pro His Ser Ile Pro Thr Pro Ile Leu
1               5                   10

<210> SEQ ID NO 95
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 95

Pro His Ser Ile Pro Thr Pro Ile Leu Ile
1               5                   10

<210> SEQ ID NO 96
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 96

His Ser Ile Pro Thr Pro Ile Leu Ile Phe
1               5                   10

<210> SEQ ID NO 97
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 97

Ser Ile Pro Thr Pro Ile Leu Ile Phe Arg
1               5                   10

<210> SEQ ID NO 98
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 98

Ile Pro Thr Pro Ile Leu Ile Phe Arg Ser
1               5                   10

```
<210> SEQ ID NO 99
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 99

Pro Thr Pro Ile Leu Ile Phe Arg Ser Pro
1               5                   10

<210> SEQ ID NO 100
<211> LENGTH: 48
<212> TYPE: PRT
<213> ORGANISM: Artificial sequence
<220> FEATURE:
<223> OTHER INFORMATION: Placental Immunoregulatory Ferritin (PLIF), C',
      derived peptide C48

<400> SEQUENCE: 100

Phe Pro Ser Pro Ile Ser Pro Ser Pro Ser Cys Trp His His Tyr Thr
1               5                   10                  15

Thr Asn Arg Pro Gln Pro Gln His His Leu Leu Arg Pro Arg Arg Arg
            20                  25                  30

Lys Arg Pro His Ser Ile Pro Thr Pro Ile Leu Ile Phe Arg Ser Pro
        35                  40                  45

<210> SEQ ID NO 101
<211> LENGTH: 27
<212> TYPE: PRT
<213> ORGANISM: Artificial sequence
<220> FEATURE:
<223> OTHER INFORMATION: monomeric synthetic peptide

<400> SEQUENCE: 101

Cys Gly His His Leu Leu Arg Pro Arg Arg Arg Lys Arg Pro His Ser
1               5                   10                  15

Ile Pro Thr Pro Ile Leu Ile Phe Arg Ser Pro
            20                  25

<210> SEQ ID NO 102
<211> LENGTH: 27
<212> TYPE: PRT
<213> ORGANISM: Artificial Sequence
<220> FEATURE:
<223> OTHER INFORMATION: dimeric synthetic peptide
<220> FEATURE:
<221> NAME/KEY: MISC_FEATURE
<222> LOCATION: (1)..(1)
<223> OTHER INFORMATION: dimerize polypeptide through double sulfide
      bond on cys number one

<400> SEQUENCE: 102

Cys Gly His His Leu Leu Arg Pro Arg Arg Arg Lys Arg Pro His Ser
1               5                   10                  15

Ile Pro Thr Pro Ile Leu Ile Phe Arg Ser Pro
            20                  25
```